United States Patent
Amano et al.

(10) Patent No.: US 7,149,568 B2
(45) Date of Patent: Dec. 12, 2006

(54) EXERCISE LOAD INTENSITY EVALUATION DEVICE AND EXERCISE EQUIPMENT

(75) Inventors: Kazuhiko Amano, Suwa (JP); Hiroaki Tanaka, Fukuoka (JP)

(73) Assignee: Seiko Epson Corporation, Tokyo (JP)

( * ) Notice: Subject to any disclaimer, the term of this patent is extended or adjusted under 35 U.S.C. 154(b) by 699 days.

(21) Appl. No.: 10/614,514

(22) Filed: Jul. 8, 2003

(65) Prior Publication Data

US 2004/0147850 A1    Jul. 29, 2004

(30) Foreign Application Priority Data

Jul. 12, 2002   (JP)   ............................. 2002-203993
Mar. 13, 2003   (JP)   ............................. 2003-068283
Mar. 13, 2003   (JP)   ............................. 2003-068284

(51) Int. Cl.
   *A61B 5/02*    (2006.01)
   *A61B 5/04*    (2006.01)
   *A61B 5/0452*  (2006.01)
   *A61B 5/024*   (2006.01)

(52) U.S. Cl. ....................... 600/513; 600/520; 600/509

(58) Field of Classification Search ................... None
See application file for complete search history.

(56) References Cited

U.S. PATENT DOCUMENTS 4,730,619 A * 3/1988 Koning et al. ................ 607/23
5,772,601 A * 6/1998 Oka et al. .................... 600/495

* cited by examiner

Primary Examiner—Carl Layno
(74) Attorney, Agent, or Firm—Oliff & Berridge, PLC

(57) ABSTRACT

An exercise load intensity evaluation device includes a pulse wave detection section which is attached to a subject during exercise and noninvasively detects a peripheral pulse wave. An ejection duration calculation section measures ejection duration from a feature of the pulse wave (dicrotic notch, for example) which reflects the cardiac ejection duration based on the detected pulse wave. The ejection duration measured at each measurement time by the ejection duration calculation section is input to an ejection duration change detection section, and the ejection duration change detection section detects a change in the ejection duration. Exercise load intensity of the subject during exercise is evaluated based on output from the ejection duration change detection section.

54 Claims, 20 Drawing Sheets

EXERCISE LOAD INTENSITY EVALUATION DEVICE AND EXERCISE EQUIPMENT

Japanese Patent Application No. 2002-203993 filed on Jul. 12, 2002, Japanese Patent Application No. 2003-68284 filed on Mar. 13, 2003, and Japanese Patent Application No. 2003-68283 filed on Mar. 13, 2003, are hereby incorporated by reference in their entirety.

BACKGROUND OF THE INVENTION

The present invention relates to an exercise load intensity evaluation device which evaluates the exercise load intensity of a subject, and to exercise equipment. More particularly, the present invention relates to an exercise load intensity evaluation device capable of evaluating whether or not current exercise load intensity is safe and effective or of evaluating the exercise load intensity, and to exercise equipment.

It is known in the art that an anaerobic threshold (AT), which represents a threshold value at which the lactate concentration in blood starts to increase (also called a threshold value at which aerobic exercise is shifted to anaerobic exercise) as exercise load intensity or oxygen intake, is an index useful for evaluating the effect of exercise on the function of the respiratory system or the circulatory system, or for selecting suitable exercise load intensity in sport training. The anaerobic threshold may be detected by detecting a lactate threshold (LT) which is exercise load intensity or oxygen intake at which the lactate concentration in blood suddenly starts to increase, or detecting a ventilatory threshold (VT) which is exercise load intensity or oxygen intake at which the rate of increase in carbon dioxide in expired air accompanied by an increase in exercise load intensity significantly increases. The anaerobic threshold approximates a catecholamine threshold (CT) at which sympathetic nervous activities are accelerated. waveform, an electrocardiophonograph, or a pulse waveform measured noninvasively. The ejection duration measurement section may include an ejection duration correction section which corrects the cardiac ejection duration based on output from a pulse waveform detection section.

The cardiac ejection duration is constant or decreases to only a small extent even if the exercise load intensity increases. However, the ejection duration significantly decreases after the exercise load intensity exceeds the lactate threshold (LT), and a definite inflection point is recognized near the lactate threshold. Therefore, if a change in the ejection duration is detected by using the ejection duration change detection section when the subject is exercising while increasing the exercise load intensity, it is possible to evaluate whether the current exercise load intensity has or has not reached the lactate threshold. For example, exercise at exercise load intensity near the lactate threshold may be defined as safe and effective exercise as an index. This exercise load intensity range may be determined based on output from the ejection duration change detection section. The exercise load intensity evaluation device of the present invention may notify the subject of this exercise load intensity by using the heart rate and power (watt).

An exercise load intensity evaluation device according to another aspect of the present invention comprises:

a diastolic time measurement section which noninvasively measures cardiac diastolic time of a subject during exercise; and a diastolic time change detection section which detects a change in the diastolic time which is measured at each measurement time by the diastolic time measurement section and is input to the diastolic time change detection section.

The diastolic time (DT) is time equivalent to a cardiac diastolic phase, and may be estimated from a feature of an electrocardiogram waveform or a pulse waveform measured noninvasively.

The cardiac diastolic time decreases as the exercise load intensity increases. However, the diastolic time is constant or changes to only a small extent after the exercise load intensity exceeds the lactate threshold (LT), and a definite inflection point is recognized near the lactate threshold. Therefore, if a change in the diastolic time is detected by using the diastolic time change detection section when the subject is exercising while increasing the exercise load intensity, it is possible to evaluate whether the current exercise load intensity has or has not reached the lactate threshold. Therefore, exercise at exercise load intensity near the lactate threshold may be defined as safe and effective exercise as an index in the same manner as in the case of the ejection duration, and this exercise load intensity range may be determined based on output from the diastolic time change detection section. The exercise load intensity evaluation device may notify the subject of this exercise load intensity by using the heart rate and power (watt).

A configuration substantially the same for the ejection duration and the diastolic time is described below.

The exercise load intensity evaluation device may further comprise an exercise load intensity measurement section which measures exercise load intensity of the subject. In this case, the ejection duration (diastolic time) change detection section may detect a change in the ejection duration (diastolic time) corresponding to different degrees of exercise load intensity based on output from the exercise load intensity measurement section. Therefore, if the ejection duration corresponding to different degrees of exercise load intensity substantially differs, or if the diastolic time corresponding to different degrees of exercise load intensity is substantially the same, the exercise may be recognized as exercise at exercise load intensity exceeding the lactate threshold.

In the exercise load intensity evaluation device of this aspect, the ejection duration (diastolic time) measurement section may further include: a body movement waveform detection section which detects a body movement waveform according to body movement of the subject during exercise; and a body movement waveform removal section which removes the body movement waveform detected by the body movement waveform detection section from the pulse wave detected by the pulse wave detection section. Since the body movement during exercise adversely influences the pulse wave, it is preferable to remove the influence of body movement. In this case, since the pulse wave from which the body movement waveform has been removed is input to the ejection duration (diastolic time) measurement section, the exercise load intensity can be evaluated with higher accuracy.

The ejection duration measurement section may measure a time interval from rise of the pulse wave to a dicrotic notch. The time interval from the rise of the pulse wave to the dicrotic notch reflects the ejection duration as described later in detail.

The diastolic time measurement section may measure the diastolic time by subtracting ejection duration from rise of the pulse wave to a dicrotic notch from one cycle of the pulse wave. The time interval from the rise of the pulse wave to the dicrotic notch reflects the ejection duration, and the sum of the ejection duration and the diastolic time equals one cycle of the pulse wave as described later in detail.

The cardiac ejection duration may be calculated from an electrocardiophonograph. Therefore, a time interval from rise of the pulse wave to the dicrotic notch may be corrected as the ejection duration from a correlation equation between systolic time obtained by measuring in advance a time interval from an aortic valve opening time S1 to an aortic valve closing time S2 by using the electrocardiophonograph and the time interval from rise of the pulse wave to the dicrotic notch.

The ejection duration (diastolic time) measurement section may include a first differentiation section which differentiates the pulse wave; and a second differentiation section which differentiates the pulse wave differentiated by the first differentiation section. Since the feature of the pulse wave described above becomes more obvious in the pulse waves differentiated by the first and the second differentiation sections, the ejection duration (diastolic time) can be measured based on these differentiated pulse waves.

The ejection duration (diastolic time) measurement section may include a comparator which compares a wave height of the pulse wave with a reference value. The ejection duration may be measured based on a pulse width of a rectangular wave output from the comparator. The diastolic time may be calculated by subtracting the ejection duration from one cycle of the pulse wave. In this case, a comparator with hysteresis and having a positive input terminal which is connected with a feed back resistor may be used. The comparator with hysteresis is capable of delaying rise of the rectangular wave even if the wave height of the pulse wave exceeds the reference value immediately after the rectangular wave falls near the dicrotic notch, for example. This enables a rectangular wave which reflects the ejection duration to be generated.

The ejection duration (diastolic time) measurement section may include a Fourier transformation section which transforms the pulse wave detected by the pulse wave detection section. In this case, the ejection duration (diastolic time) measurement section may extract a frequency spectrum which is obtained based on the feature of the pulse wave which reflects the cardiac ejection duration (diastolic time) from Fourier transformed frequency spectra. The ejection duration (diastolic time) change detection section may detect a change in frequency of the frequency spectrum extracted at each measurement time by the ejection duration (diastolic time) measurement section. This enables the change in the ejection duration (diastolic time) to be detected based on the frequency spectrum.

The ejection duration (diastolic time) measurement section may further includes: a first Fourier transformation section which transforms the pulse wave detected by the pulse wave detection section; and a second Fourier transformation section which transforms the body movement waveform detected by the body movement waveform detection section. In this case, the body movement waveform removal section may subtract frequency spectra at the same frequency among frequency spectra in each frequency band output from the first and second Fourier transformation sections. This enables the body movement to be removed at the stage of the frequency spectrum. The subsequent detection of the ejection duration (diastolic time) and the change in the ejection duration (diastolic time) may be performed based on the frequency spectrum in the same manner as described above.

The ejection duration (diastolic time) measurement section may include an inverse Fourier transformation section which performs inverse Fourier transformation of output from the body movement waveform removal section, and measure a time interval from rise of the inverse Fourier transformed pulse wave to a dicrotic notch. The ejection duration (diastolic time) measurement section may include a first differentiation section which differentiates the pulse wave which has been inverse-Fourier-transformed; and a second differentiation section which differentiates the pulse wave differentiated by the first differentiation section, and measures the ejection duration (diastolic time) based on the pulse wave differentiated by the first or second differentiation section.

The exercise load intensity evaluation device of the present invention may further comprise a notification section which notifies the subject that the exercise is anaerobic exercise at an exercise load intensity exceeding the lactate threshold based on output from the ejection duration (diastolic time) change detection section. This enables the subject to continue exercising at exercise load intensity near the lactate threshold. It suffices that the subject maintain the exercise load intensity constant when notified from the notification section.

The notification section may notify the subject of a heart rate calculated from one cycle of the heartbeat output from the ejection duration (diastolic time) change detection section.

An exercise load intensity evaluation device according to another aspect of the present invention comprises an exercise load intensity detection section which detects exercise load intensity from a storage section based on the ejection duration (diastolic time) measured by the ejection duration (diastolic time) measurement section instead of, or in addition to, the ejection duration (diastolic time) change detection section. The correlation data between the cardiac ejection duration (diastolic time) and the exercise load intensity of the subject is stored in advance in the storage section. This enables the exercise load intensity to be recognized during exercise.

The exercise load intensity detection section may detect the exercise load intensity when the ejection duration (diastolic time) change detection section detects that the ejection duration (diastolic time) is changed.

In the present invention, a ratio of the ejection duration (diastolic time) to one cycle of a heartbeat (hereinafter called "normalized ejection duration (diastolic time)") may be used instead of the ejection duration (diastolic time). One cycle of the heartbeat decreases at a constant rate as the exercise load intensity increases, irrespective of the lactate threshold LT. On the contrary, the rate of change in the ejection duration differs across the lactate threshold LT as shown in FIG. 2 as described later. Therefore, the normalized ejection duration decreases in proportion to the rate of decrease in one cycle of the heartbeat as the exercise load intensity increases until the exercise load intensity reaches the lactate threshold LT. The rate of decrease in the normalized ejection duration significantly decreases after the exercise load intensity has reached the lactate threshold LT. On the contrary, the rate of change in the diastolic time differs across the lactate threshold LT as shown in FIG. 16 as described below. Therefore, the normalized diastolic time decreases as the exercise load intensity increases until the exercise load intensity reaches the lactate threshold LT. However, the rate of decrease in the normalized diastolic time is almost constant or increases to only a small extent irrespective of a decrease in one cycle of the heartbeat or pulse wave after the exercise load intensity has reached the lactate threshold LT. The subject can be notified that the exercise load intensity has reached the lactate threshold LT, or of the exercise load intensity and safety during exercise from the normalized ejection duration in each of the above aspects.

The notification section may notify the subject that the exercise load intensity is out of a safety exercise range by setting an ejection duration (diastolic time) exceeding the safe exercise range in a storage section in advance, and comparing the measured ejection duration (diastolic time) with the ejection duration (diastolic time) stored in the storage section.

Exercise equipment according to a further aspect of the present invention comprises the exercise load intensity evaluation device. The exercise equipment may output exercise menus of different degrees of exercise load intensity on a display section or the like, or change the exercise load intensity that is applied to the subject by using a load output section according to the exercise menu. For example, a belt velocity of a running/walking machine or pedal load of a pedal machine may be changed. The exercise load intensity and the cardiac ejection duration (diastolic time) may be measured in advance for each subject, and a safe and effective exercise menu may be set to the exercise equipment for each subject. A safe and effective exercise menu is set within a predetermined exercise load intensity range based on the lactate threshold calculated in advance for each subject from the correlation between the exercise load intensity and the ejection duration (diastolic time). The exercise load intensity range may be set near the lactate threshold for a person suffering from heart disease and a healthy person, for example. However, the exercise load intensity range may be set in a range temporarily exceeding the lactate threshold if the ejection duration decreases to only a small extent or further decreases. The exercise load intensity range may be set in a range exceeding the lactate threshold for an athlete, for example. The exercise load intensity range may be set as a range of the heart rate based on one cycle of the heartbeat output from the ejection duration (diastolic time) change detection section. An exercise menu suitable for a subject can be easily set if a storage medium which stores the exercise menu can be removed from the exercise equipment.

DETAILED DESCRIPTION OF THE EMBODIMENT

An embodiment of the present invention is described below with reference to the drawings.

Description of Ejection Duration and Diastolic Time

Figure 1:
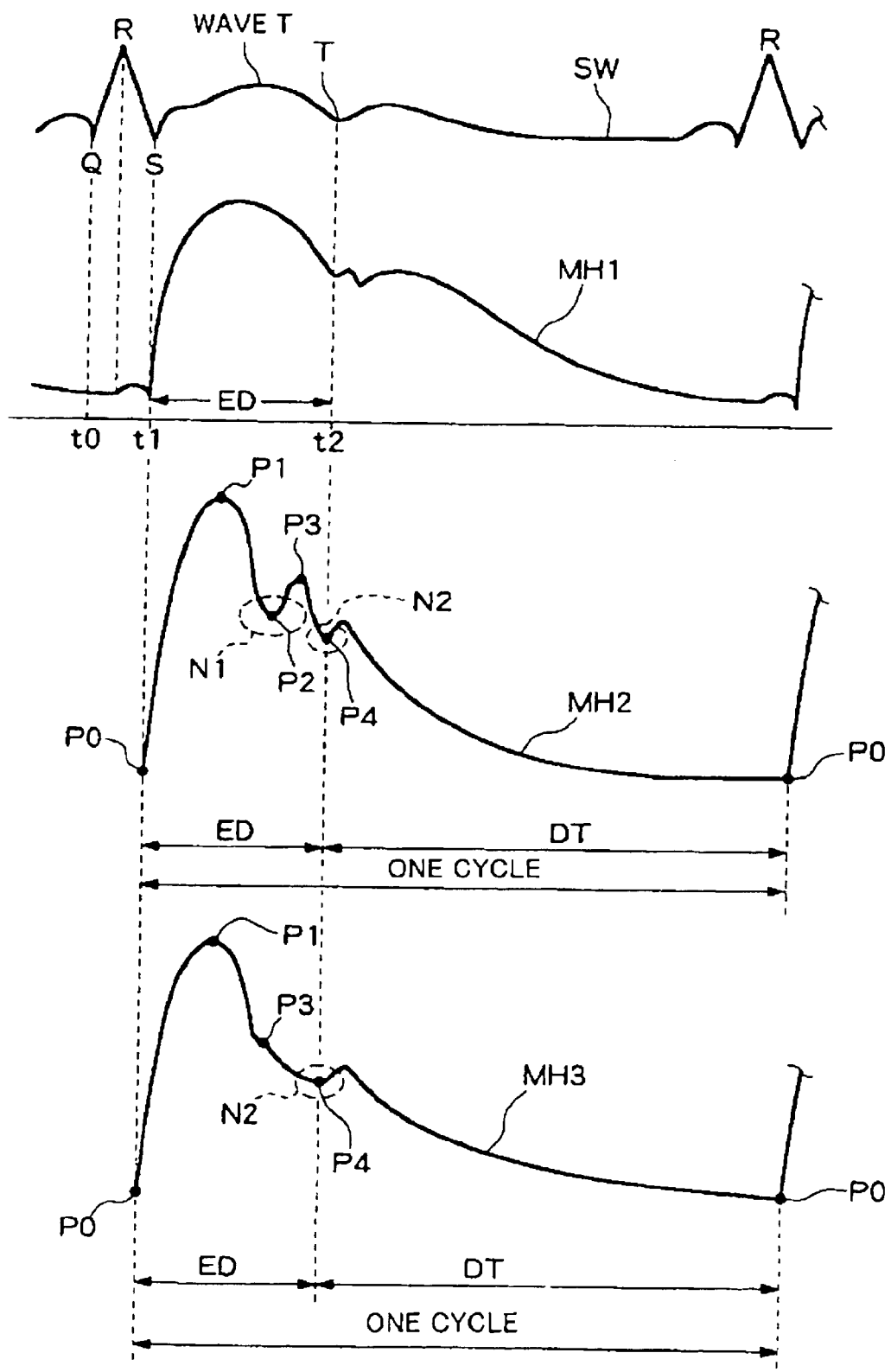
FIG. 1 shows the relation between a pulse waveform immediately after blood flows out from the heart and a peripheral pulse waveform.

FIG. 1 shows a cardiac cycle. In FIG. 1, a waveform SW is an electrocardiogram waveform, a waveform MH1 is an aortic pressure waveform immediately after blood flows out from the heart, and a waveform MH2 is a peripheral (radial artery) pulse waveform. In FIG. 1, time delay caused by blood flow is not taken into consideration. The ejection duration (ED) is a time interval from an aortic valve opening time t1 to an aortic valve closing time t2 in the aortic pressure waveform MH1 in the strict sense. The ejection duration is about 280 ms after resting. Since the aortic valve is opened by contraction of a ventricle, the ejection duration approximately corresponds to systolic time (time Q-T in the electrocardiogram waveform SW in FIG. 1). The systolic time is divided into an isovolumetric contraction period and the ejection duration. The isovolumetric contraction period is a time interval from the start of electrical systole to the opening of the aortic valve.

The cardiac diastolic time DT is duration of the ventricular diastole. The isovolumetric contraction period, the ejection duration ED, and the diastolic time DT have a relation expressed by "isovolumetric contraction period+ejection duration ED+diastolic time DT=one cycle of heartbeat or pulse wave (time R—R in the electrocardiogram waveform SW or time P0—P0 in the pulse waveform MH2 in FIG. 1, for example)". The diastolic time DT may be calculated by directly measuring the cardiac sound, or may be calculated by subtracting the ejection duration ED from one cycle of the heartbeat or pulse wave.

A notch N2 in the peripheral pulse waveform MH2 occurs due to the closing of the aortic valve. Therefore, a time interval from a minimum peak P0 to a peak P4 which occurs immediately after a maximum peak P1 in the pulse waveform MH2 is called the estimated systolic time. The ejection duration ED may be estimated from the estimated systolic time.

It is known that the pulse waveform has individual variation and the waveform changes depending on the physical condition. Therefore, there may be a case where the peak P2 overlaps the peak P3 and a notch N1 does not occur as shown in a waveform MH3 differing from the peripheral pulse waveform MH2. In the present embodiment, the time interval from the point P0 to the dicrotic notch P4 is taken as the ejection duration ED irrespective of the type of the pulse waveforms MH2 and MH3 shown in FIG. 1.

The following description is given on the premise that the ejection duration ED also includes the systolic time and the estimated systolic time.

The cardiac ejection duration may be estimated from the feature of the electrocardiogram waveform or the pulse wave as described above. The following description illustrates the case where the ejection duration is estimated from the pulse wave. However, the ejection duration may be estimated from the electrocardiogram waveform by using an electrocardiogram measurement section. In the electrocardiogram waveform SW in FIG. 1, inflection points Q and T may be determined based on a wave Q, and time Q-T may be estimated as the systolic time. The systolic time is "isovolumetric contraction period+ejection duration" in the strict sense. However, the systolic time may be estimated as the ejection duration.

Correlation Between Ejection Duration or Diastolic Time and Amount of Lactate

Figure 2:
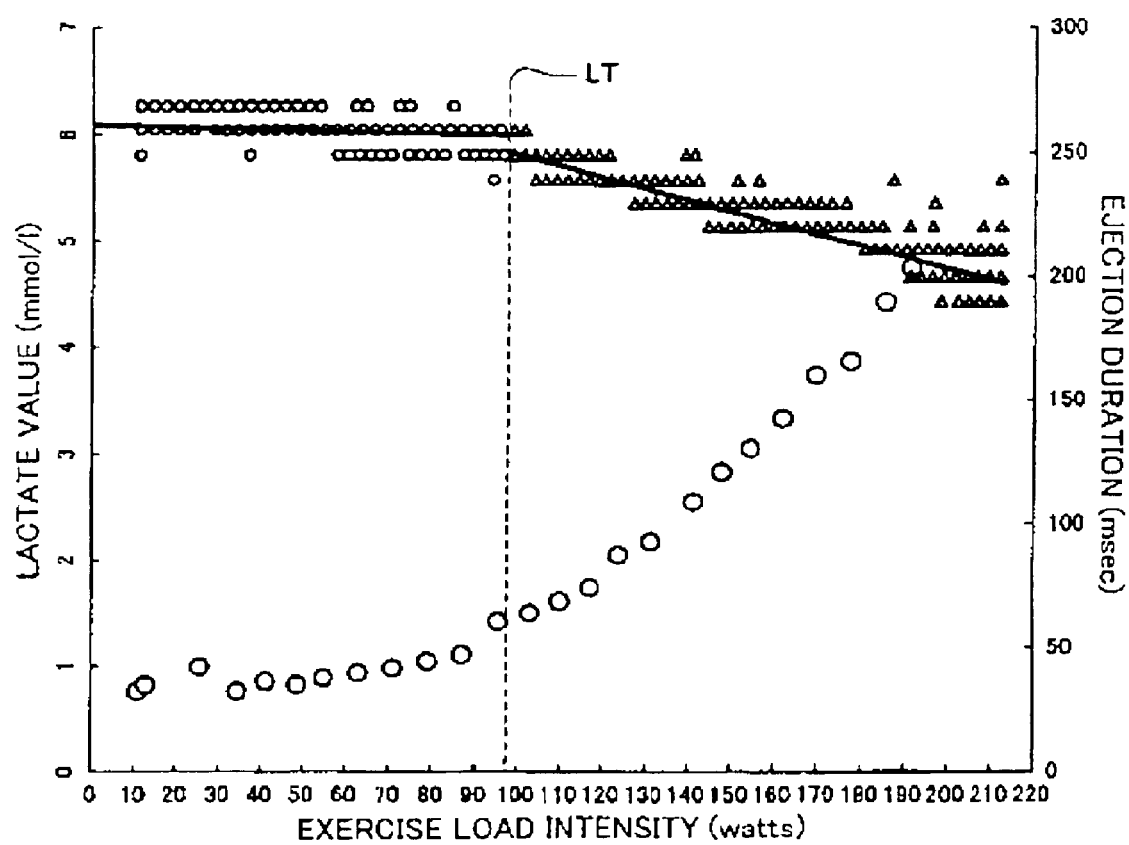
FIG. 2 is a characteristic diagram showing the relation among exercise load intensity, the amount of lactate in blood, and ejection duration.

FIG. 2 is a characteristic diagram showing the correlation between the ejection duration and the lactate value of a subject with respect to exercise load intensity. In FIG. 2, the horizontal axis indicates exercise load intensity (watt), the left vertical axis indicates the ejection duration (msec), and the right vertical axis indicates the lactate value (mmol/l) in the blood.

The correlation between the lactate value in the blood and the degree of fatigue corresponding to the exercise load intensity is known. In FIG. 2, the lactate value in the blood increases as the exercise load intensity increases.

If the exercise load intensity is small, the degree of fatigue is small and the amount of lactate in the blood does not considerably increase.

Exercise optimum for a human body is continuous exercise at an intensity of the lactate threshold LT or the catecholamine threshold CT at which sympathetic nervous activities are accelerated. Therefore, it is extremely useful to know exercise load intensity corresponding to the lactate threshold LT or the catecholamine threshold CT based on the ejection duration detected noninvasively.

As shown in FIG. 2, the ejection duration ED is changed to only a small extent and a change in the lactate value in the blood is small at an exercise load intensity equal to or less than about 100 watts. However, the ejection duration ED decreases and the rate of change in the lactate value in blood increases after the exercise load intensity exceeds 100 watts. The lactate threshold LT of this subject is an exercise load intensity of about 100 watts.

If the ejection duration ED is monitored during exercise, and the ejection duration ED is substantially constant, the exercise load intensity is determined to be equal to or lower than the lactate threshold LT. If the ejection duration ED substantially exceeds the constant value, the exercise load intensity is determined to reach the lactate threshold LT. Therefore, it is possible to direct the subject to maintain the exercise load intensity.

Figure 16:
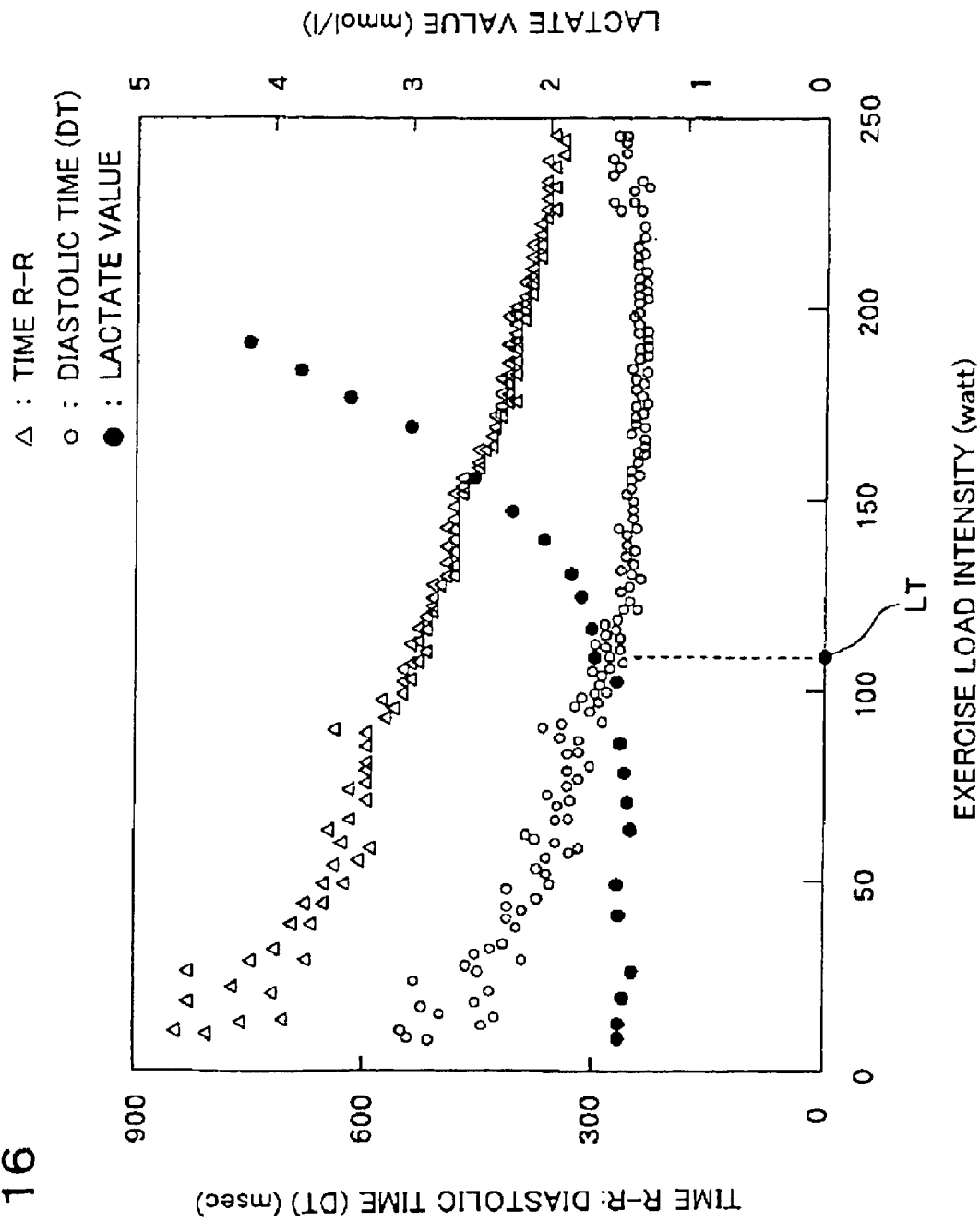
FIG. 16 is a characteristic diagram showing the relation among exercise load intensity, the amount of lactate in blood, diastolic time, and one cycle of a heartbeat.

FIG. 16 is a characteristic diagram showing the correlation between the diastolic time DT, the ejection duration ED, and one cycle (time R—R) of the pulse wave or heartbeat, and the lactate value of a subject with respect to exercise load intensity. In FIG. 16, the horizontal axis indicates the exercise load intensity (watt), the left vertical axis indicates time (msec), and the right vertical axis indicates the lactate value (mmol/l) in the blood.

It is known that the time R—R shown in FIG. 16 decreases at an approximately constant rate as the exercise load intensity increases. As shown in FIG. 16, the diastolic time DT decreases at a rate approximately the same as that of the time R—R before the exercise load intensity reaches the lactate threshold LT. However, the diastolic time DT is changed to only a small extent after the exercise load intensity exceeds the lactate threshold LT. The ejection duration ED is the difference between the time R—R and (isovolumetric contraction period+diastolic time DT). As shown in FIG. 16, the ejection duration ED is changed to only a small extent before the exercise load intensity reaches the lactate threshold LT, and decreases at a rate approximately the same as that of the time R—R after the exercise load intensity exceeds the lactate threshold LT. Exercise optimum for a human body is continuous exercise at an intensity of the lactate threshold LT or the catecholamine threshold CT at which sympathetic nervous activities are accelerated. Therefore, it is extremely useful to know exercise load intensity corresponding to the lactate threshold LT or the catecholamine threshold CT based on the ejection duration detected noninvasively.

As shown in FIG. 16, if the exercise load intensity is about 100 watts or less, the ejection duration ED is changed to only a small extent, the diastolic time DT decreases at a rate approximately the same as that of the time R—R, and a change in the lactate value in the blood is small. However, if the exercise load intensity exceeds 100 watts, the ejection duration ED decreases, the diastolic time DT is changed to only a small extent, and the rate of change in the lactate value in the blood increases. The lactate threshold LT of this subject is an exercise load intensity of about 100 watts.

If the diastolic time DT is monitored during exercise while changing the exercise load intensity, the exercise load intensity is determined to be equal to or less than the lactate threshold LT if the diastolic time DT is changed. The exercise load intensity is determined to reach the lactate threshold LT if the diastolic time DT is not substantially changed. Therefore, it is possible to direct the subject to maintain the exercise load intensity.

Figure 3:
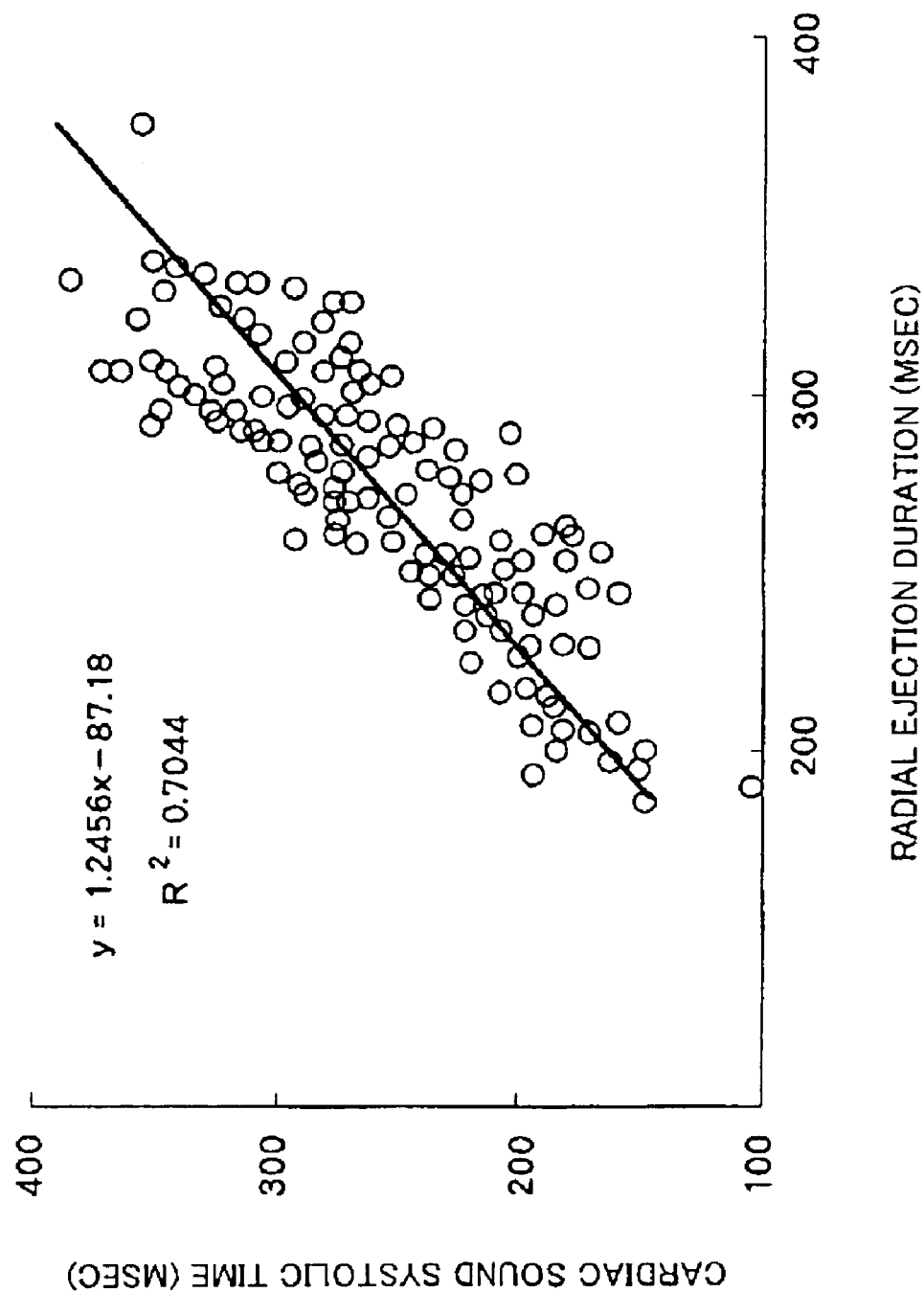
FIG. 3 is a characteristic diagram showing the relation between radial ejection duration and cardiac sound systolic time.

FIG. 3 is a characteristic diagram showing the relation between the radial ejection duration and the cardiac sound systolic time of six subjects. The radial ejection duration is a time interval from rise of the radial artery pulse wave to the dicrotic notch. The cardiac sound systolic time is a value obtained by measuring the systolic time at a time interval from a first sound to a second sound in the phonocardiogram. In FIG. 3, the horizontal axis indicates the radial ejection duration (msec), and the vertical axis indicates the cardiac sound systolic time (msec). As shown in FIG. 3, the correlation between the radial ejection duration and the cardiac sound systolic time is approximated by $y=1.2456x-87.18$ provided that the square of the correlation coefficient R equals 0.7044 (coefficient of determination). This enables the ejection duration calculated from the peripheral pulse wave to be corrected as the central ejection duration. A correction section may be provided to an ejection duration calculation section 90 shown in FIG. 4 or a diastolic time calculation section 91 shown in FIG. 17 as described later. The coefficient of the above linear equation may be calculated in advance for each subject from the phonocardiogram or the like instead of using a general equation.

Outline of Exercise Load Intensity Evaluation Device

Figure 4:
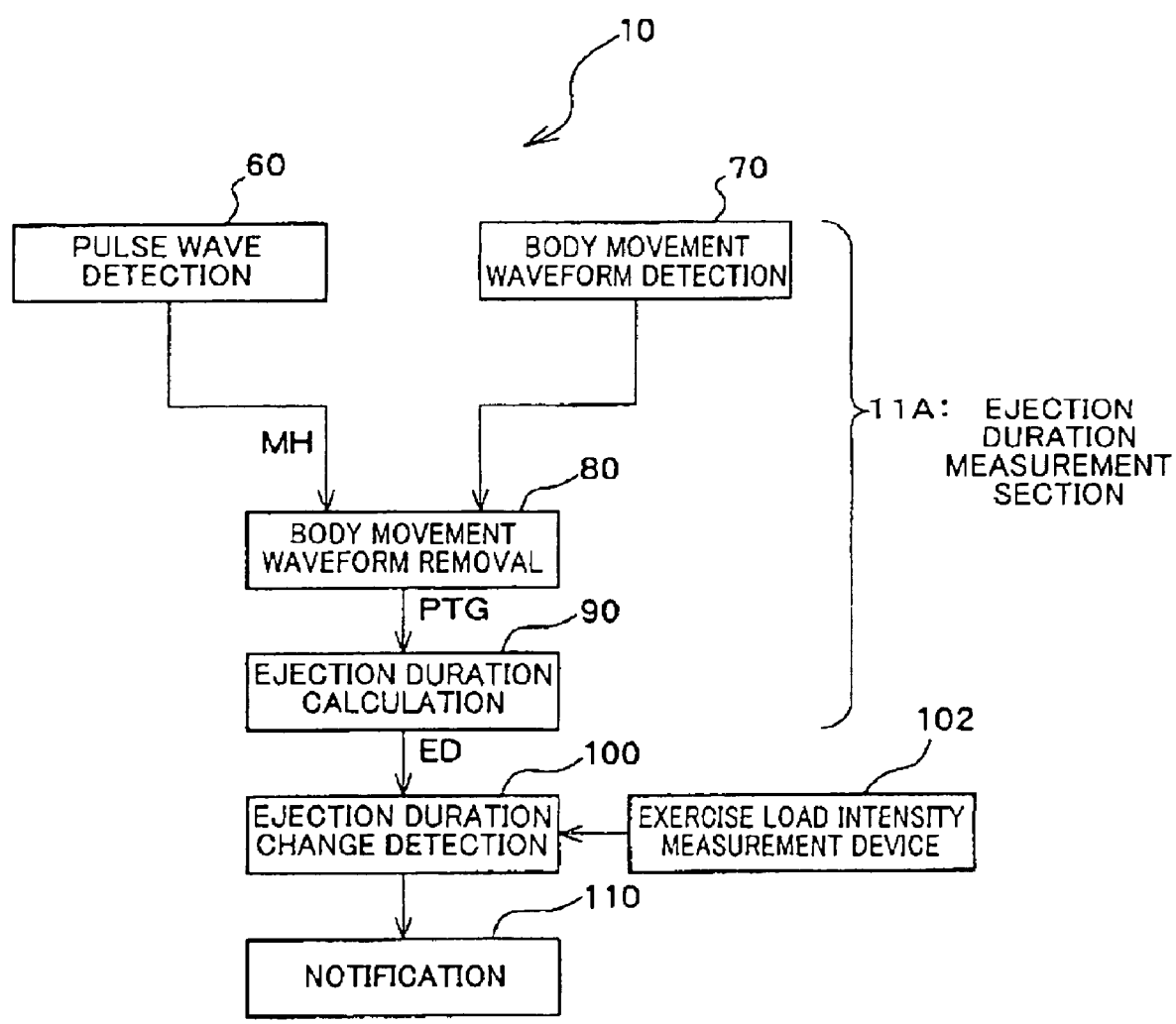
FIG. 4 is a block diagram showing an exercise load intensity evaluation device according to an embodiment of the present invention.
Figure 17:
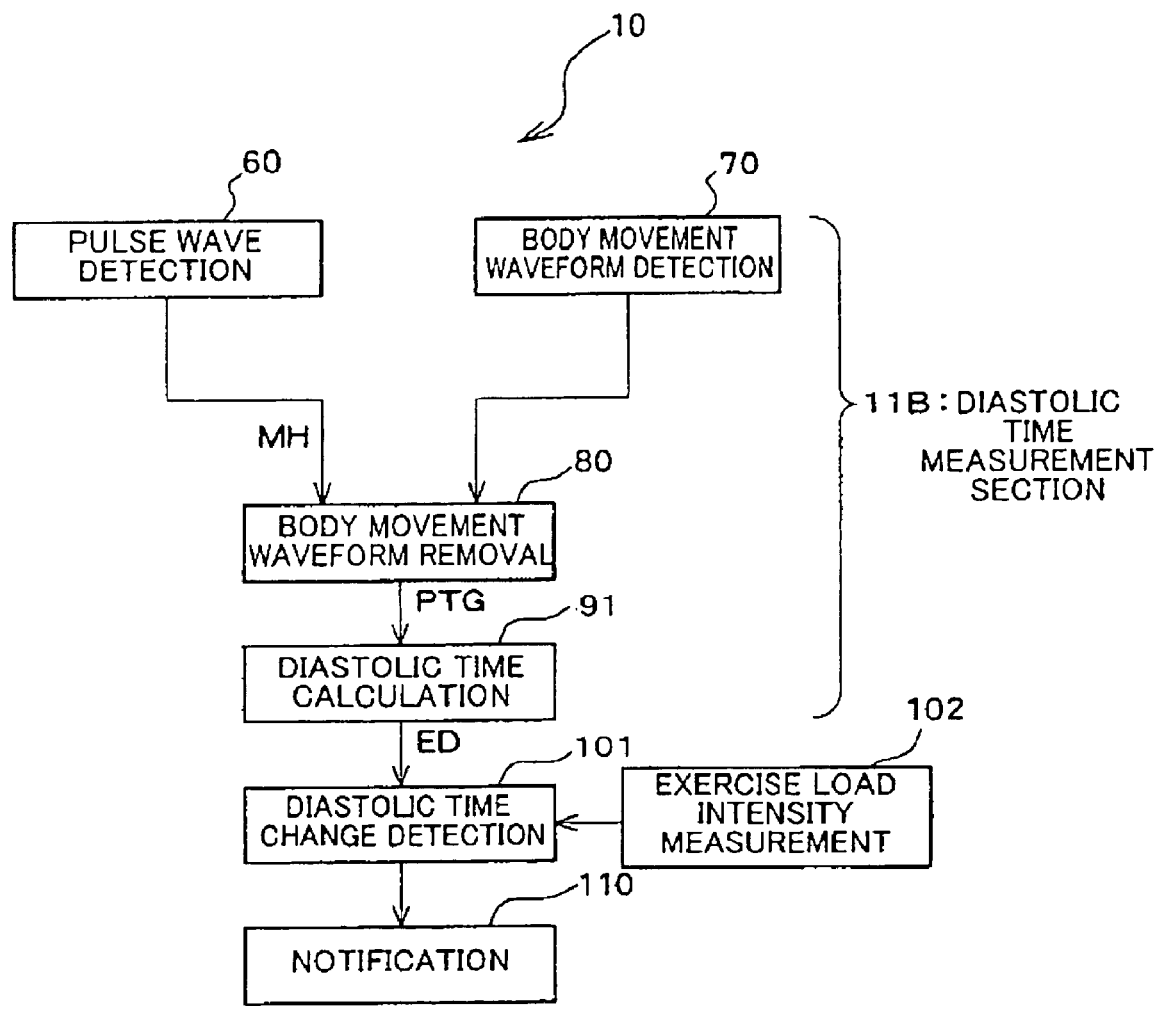
FIG. 17 is a block diagram showing an exercise load intensity evaluation device according to another embodiment of the present invention.

An exercise load intensity evaluation device in the present embodiment evaluates the exercise load intensity of a subject based on the above-described principle, and has a configuration shown in a block diagram of FIG. 4 or 17. An exercise load intensity evaluation device 10 shown in FIG. 4 includes a pulse wave detection section 60, a body movement waveform detection section 70, a body movement waveform removal section 80, an ejection duration calculation section 90, an ejection duration change detection section 100, and a notification section 110. In the present embodiment, the pulse wave detection section 60, the body movement waveform detection section 70, the body movement waveform removal section 80, and the ejection duration calculation section 90 make up an ejection duration measurement section 11. In FIG. 17, a diastolic time calculation section 91 and a diastolic time change detection section 101 are provided instead of the ejection duration calculation section 90 and the ejection duration change detection section 100 shown in FIG. 16.

The pulse wave detection section 60 noninvasively detects the peripheral pulse wave of a subject. The body movement waveform detection section 70 detects a body movement waveform according to the body movement of the subject during exercise, and may be formed by using an acceleration sensor, for example. The body movement waveform removal section 80 removes the body movement waveform detected by the body movement waveform detection section 70 from the pulse wave detected by the pulse wave detection section 60. The ejection duration calculation section 90 calculates the time interval (ejection duration ED) from the peak P0 to the peak P4 from the pulse wave (radial pulse wave MH2 or MH3 shown in FIG. 1, for example) from which the body movement waveform has been removed. A time interval of one cycle of the pulse wave and the ejection duration ED measured at each measurement time by the ejection duration calculation section 90 are input to the ejection duration change detection section 100, and the ejection duration change detection section 100 detects a change in the ejection duration ED. The ejection duration change detection section 100 outputs the heart rate when the ejection duration ED is changed. Since the ejection duration ED is changed if the subject is exercising at an exercise load intensity exceeding the lactate threshold LT shown in FIG. 2, the ejection duration change detection section 100 detects the change in the ejection duration ED. The notification section 110 is informed of the heart rate at the exercise load intensity near the lactate threshold LT when the ejection duration change detection section 100 detects the change in the ejection duration. The notification section 110 notifies the subject of the heart rate when the ejection duration ED is changed in addition to the change in the ejection duration.

The diastolic time calculation section 91 shown in FIG. 17 calculates one cycle of the pulse wave from the peak P0 to the next peak P0 (time R—R) and the ejection duration ED from the peak P0 to the peak P4 from the pulse wave (radial pulse wave MH2 or MH3 shown in FIG. 1, for example) from which the body movement waveform is removed, and calculates the diastolic time DT from the difference between one cycle of the pulse wave and the ejection duration ED. A time interval of one cycle of the pulse wave and the diastolic time DT measured at each measurement time by the diastolic time calculation section 91 are input to the diastolic time change detection section 101, and the diastolic time change detection section 101 detects a change in the diastolic time DT. The diastolic time change detection section 101 outputs the heart rate when the diastolic time DT becomes substantially constant. Since the diastolic time DT is substantially constant or decreases to only a small extent if the subject is exercising at an exercise load intensity exceeding the lactate threshold LT shown in FIG. 16, whether or not the exercise load intensity has reached the lactate threshold LT can be detected. The notification section 110 shown in FIG. 17 is informed of the heart rate at the exercise load intensity near the lactate threshold LT when the diastolic time DT becomes substantially constant. The notification section 110 notifies the subject of the heart rate when the diastolic time becomes substantially constant in addition to the change in the diastolic time.

The subject can detect that the exercise load intensity is near the lactate threshold LT by the notification from the notification section 110 shown in FIG. 4 or 17. Therefore, the subject can continuously exercise at an exercise load intensity near the lactate threshold LT by maintaining the exercise load intensity after the notification. It is useful to notify the subject of the heart rate when the diastolic time becomes substantially constant. The subject can continue safe and effective exercise by setting the heart rate when the diastolic time becomes substantially constant as the upper limit and setting 90% of the upper limit as the lower limit, for example.

As shown in FIG. 4 or 17, the exercise load intensity evaluation device 10 may further include an exercise load intensity measurement section 102 which measures the exercise load intensity of the subject. Output from the exercise load intensity measurement section 102 is input to the ejection duration change detection section 100 or the diastolic time change detection section 101. Therefore, the ejection duration change detection section 100 or the diastolic time change detection section 101 may be formed to detect the change in the ejection duration or the diastolic time corresponding to different degrees of exercise load intensity, and not to detect the change in the ejection duration or the diastolic time if the exercise load intensity is not changed. Therefore, the ejection duration change detection section 100 or the diastolic time change detection section 101 can detect the change in the ejection duration or the diastolic time corresponding to different degrees of exercise load intensity.

External Configuration of Exercise Load Intensity Evaluation Device

Figure 5A:
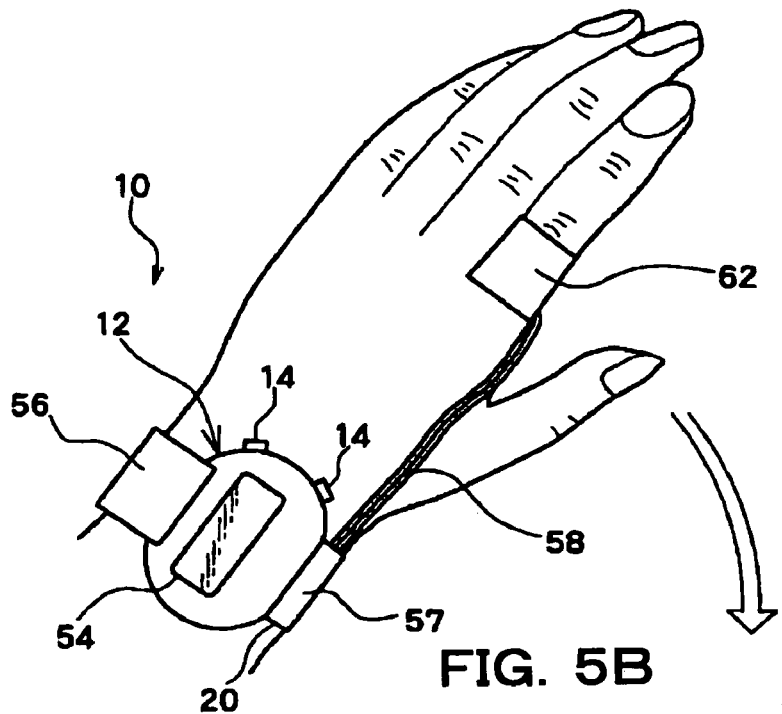
FIGS. 5A to 5C are external views of an exercise load intensity evaluation device according to an embodiment of the present invention.
Figure 5B:
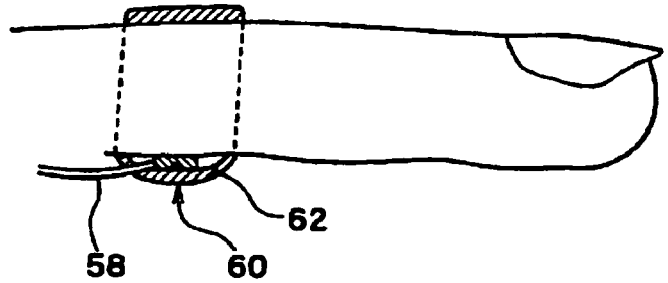
Figure 5C:
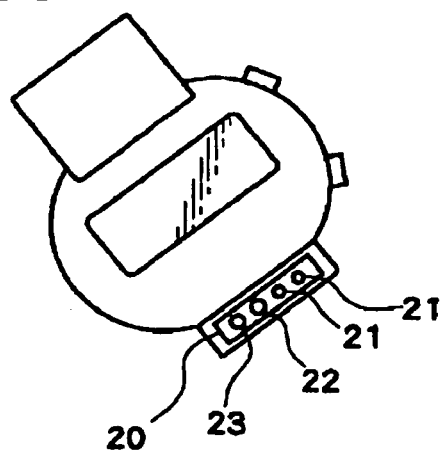

The exercise load intensity evaluation device in the present embodiment may have an external configuration shown in FIGS. 5A, 5B, and 5C, for example. However, the external configuration is not limited to that shown in FIGS. 5A, 5B, and 5C. The exercise load intensity evaluation device 10 includes a body 12 having a structure in the shape of a wristwatch, a cable 58 connected to a connector section 20 of the body 12 through a connector piece 57, and the pulse wave detection section 60 provided on the end of the cable 58. A wrist band 56 is attached to the body 12, and the body 12 is installed on the wrist of a subject by using the wrist band 56.

The body 12 includes the connector section 20. The connector piece 57, which is the end of the cable 58, is removably provided to the connector section 20.

FIG. 5C shows the connector section 20 from which the connector piece 57 is removed. The connector section 20 includes connection pins 21 for connecting with the cable 58, and an LED 22 and a phototransistor 23 for transferring data, for example.

A display section 54 such as a liquid crystal panel is provided on the surface side of the body 12 as an example of the notification section 110. The display section 54 has a segment display region and a dot display region, and displays evaluation results for exercise load intensity. A display device other than a liquid crystal panel may be used as the display section 54.

The body 12 includes a central processing unit (CPU) which controls various types of calculations and conversions, and a memory which stores a program for operating the CPU and the like (not shown). Button switches 14 for performing various types of operations and input are provided on the periphery of the body 12.

The pulse wave detection section 60 is installed near the root of the forefinger of a subject while being shaded by a sensor securing band 62, as shown in FIG. 5B. Since a long cable 58 is made unnecessary by installing the pulse wave detection section 60 near the root of the finger, the subject is not disturbed if the cable 58 is installed. Moreover, since the change in blood flow due to temperature is small near the root of the finger in comparison with the fingertip, the pulse waveform to be detected is less influenced by temperature or the like.

Pulse Wave Detection Section

Figure 6:
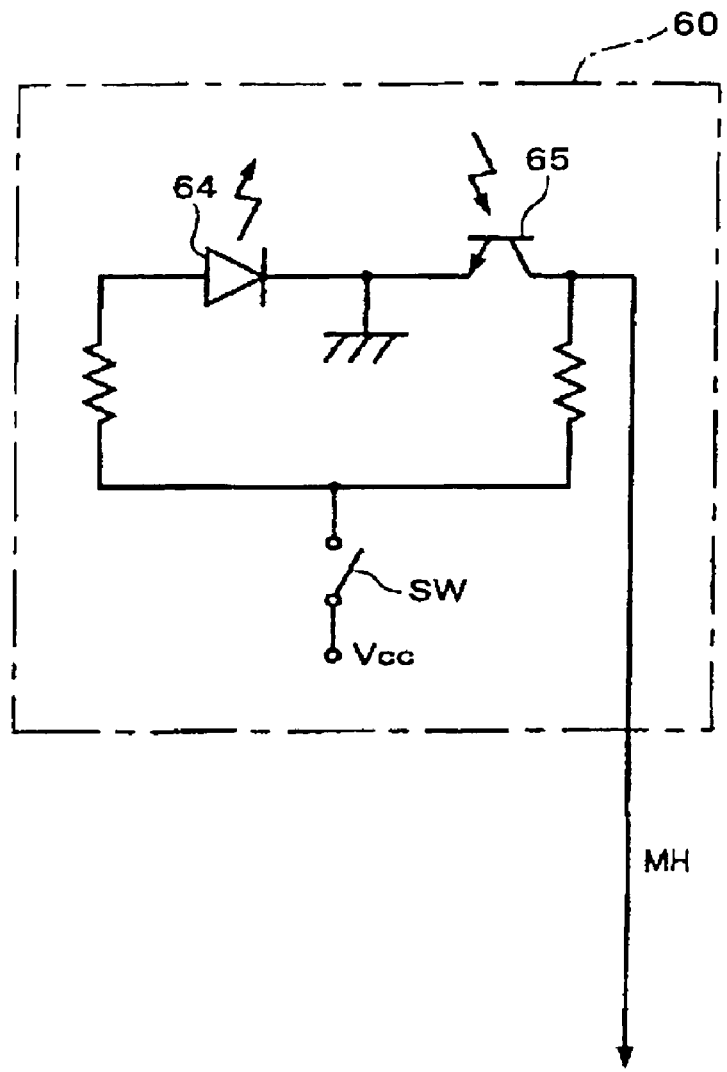
FIG. 6 is a circuit diagram showing an example of a circuit configuration of a pulse wave detection section shown in FIG. 5B.

As shown in FIG. 6, the pulse wave detection section 60 includes an LED 64 and a phototransistor 65, and is formed so that the peripheral pulse wave can be detected noninvasively, specifically, without breaking the skin. The pulse wave detection section 60 utilizes a phenomenon in which the pulse waveform is almost the same as the waveform of the change in blood flow (plethysmogram waveform), and detects the pulse wave (plethysmogram) by using a photosensor formed to emit light to a capillary plexus and to detect the change in the amount of light reflected by or transmitted through blood in the capillary blood vessel.

In more detail, when a switch SW is turned on and a power supply voltage is applied, light is emitted from the LED 64 of the pulse wave detection section 60. The emitted light is reflected by a blood vessel or tissue of a subject and received by the phototransistor 65. Therefore, a photocurrent of the phototransistor 65 is converted into a voltage and output as a signal MH of the pulse wave detection section 60. An LD may be used instead of the LED 64.

The emission wavelength of the LED 64 is selected within the absorption wavelength of hemoglobin in blood. In the present embodiment, the emission wavelength of the LED 64 is selected near the peak of the absorption wavelength of hemoglobin. Therefore, the light receiving level is changed corresponding to the blood flow. Therefore, the pulse waveform is detected by detecting the light receiving level. As the LED 64, an InGaN (indium-gallium-nitrogen) based blue LED is suitably used, for example. The emission spectrum of the LED may have an emission peak of about 450 nm, and the emission wavelength region of the LED may be 350 to 600 nm. However, the emission wavelength region of the LED may be a near-infrared wavelength region.

In the present embodiment, a GaAsP (gallium-arsenic-phosphorus) based phototransistor may be used as the phototransistor 65 corresponding to the LED having the above emission characteristics. The phototransistor 65 may have a main sensitivity region at 300–600 nm, and also have a sensitivity region at 300 nm or less.

The pulse wave can be detected in a wavelength region of 300–600 nm by combining the blue LED 64 with the phototransistor 65. This contributes to the following advantages.

Light having a wavelength region of 700 nm or less contained in external light is rarely transmitted through the tissue of the finger, and does not reach the phototransistor 65 through the tissue of the finger even if external light is applied to the finger in the area in which the finger is not covered with the sensor securing band. As a result, only light having a wavelength region which does not influence the detection of the pulse wave reaches the phototransistor 65. Light having a wavelength region greater than 300 nm is almost completely absorbed on the surface of the skin. Therefore, the substantial light receiving wavelength region becomes 300–700 nm even if the light receiving wavelength region is set at 700 nm or less. Therefore, the influence of external light can be prevented without entirely covering the finger. Hemoglobin in blood has a large absorption coefficient for light having a wavelength of 300–700 nm, which is several to about one hundred times or more greater than the absorption coefficient for light having a wavelength of 880 nm. Therefore, if light having a wavelength region for which the absorption coefficient of hemoglobin is great (300–700 nm) is used as the detection light as in this example, since the detected value changes with high sensitivity corresponding to the change in blood flow, the SN ratio of the pulse waveform based on the change in blood flow may increase.

The pulse wave detection section 60 takes the pulse wave which changes corresponding to blood flow (plethysmogram) as the change in the amount of erythrocytes in the capillary plexus present near the skin, and detects the pulse wave as the change in the amount of transmission or reflection of light applied to the skin. Therefore, the pulse wave can be detected without placing the sensor at the position of the peripheral artery such as the radial artery or digital artery. The pulse wave detection section 60 is capable of stably detecting the change in the amount of erythrocytes in the capillary blood vessel present near the skin as the pulse wave (plethysmogram) in the peripheral artery. Therefore, light having a near-infrared wavelength region (880 nm or more) which has good transmissivity to the subcutaneous tissue and for which hemoglobin has absorption characteristics may also be employed. The pulse wave detection section 60 may detect the pulse wave based on the pulse pressure. The pulse wave detection section 60 may be attached to a part other than the finger. For example, the pulse wave detection section 60 may detect the pulse wave from the ear.

First Configuration Example of Ejection Duration Measurement Section or Diastolic Time Measurement Section The ejection duration ED is the time interval from the rising point P0 of the pulse wave to the dicrotic notch P4 in the pulse waveform MH2 or MH3 as described with reference to FIG. 1.

Figure 7:
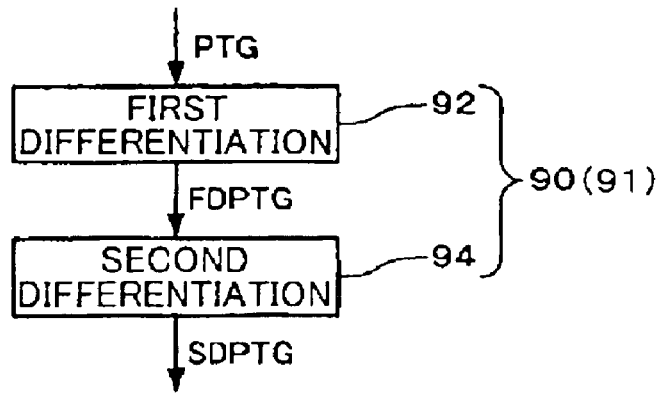
FIG. 7 is a block diagram showing an ejection duration measurement section including first and second differentiation circuits.

The points P0 and P4 may be directly calculated from the pulse waveform MH. However, the location of the inflection points P0 and P4 in the pulse waveform becomes more obvious by calculating an acceleration waveform obtained by differentiating the pulse waveform twice. As shown in FIG. 7, the ejection duration calculation section 90 and the diastolic time calculation section 91 include a first differentiation section 92 which differentiates the pulse wave PTG (first differentiation waveform FDPTG) output from the body movement waveform removal section 80, and a second differentiation section 94 which differentiates the first differentiation waveform FDPTG. The ejection duration calculation section 90 and the diastolic time calculation section 91 may include only the first differentiation section 92 which differentiates the pulse wave PTG.

Figure 8:
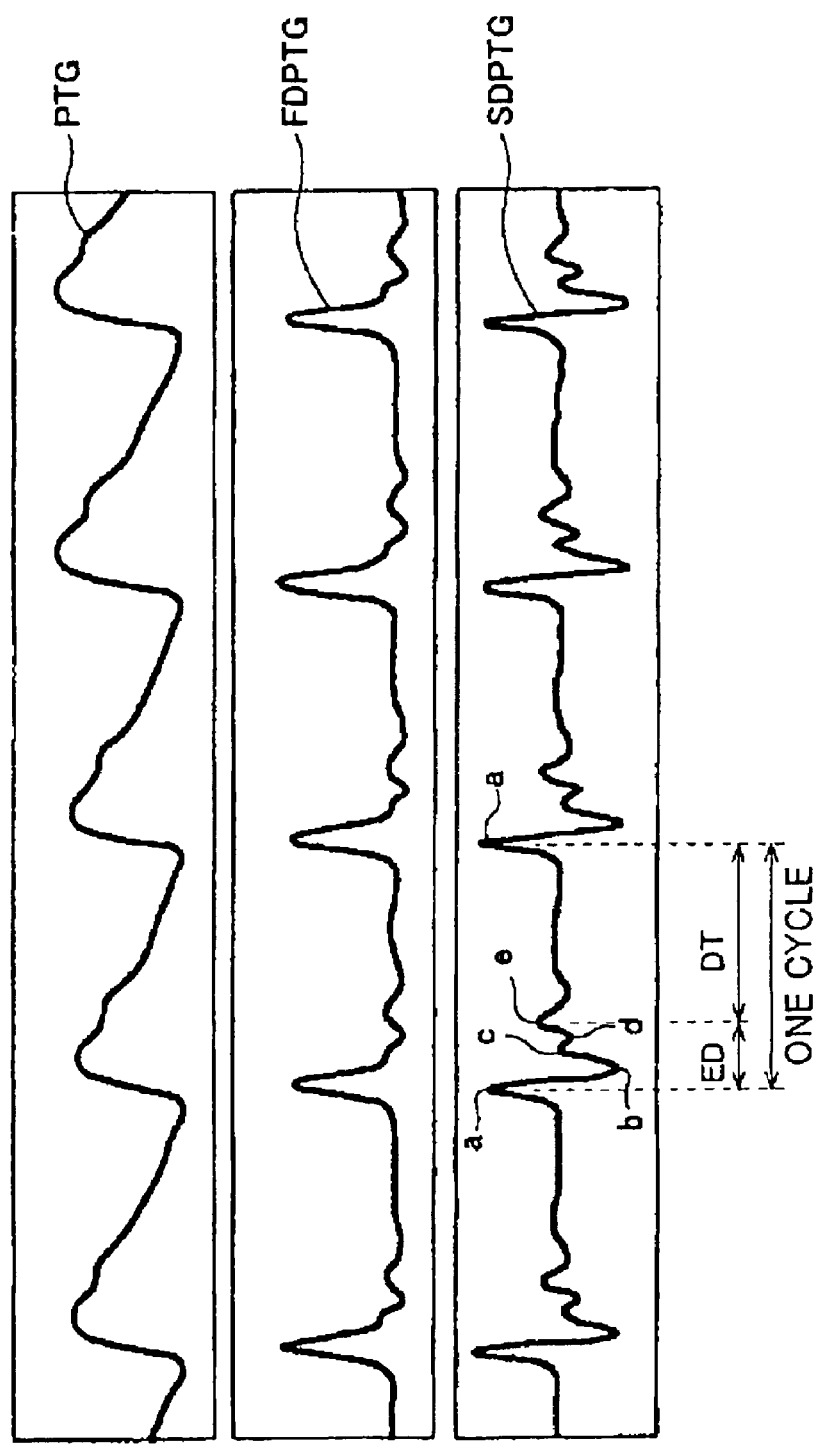
FIG. 8A is a waveform diagram showing an original pulse waveform PTG from which a body movement waveform has been removed.
FIG. 8B is a waveform diagram showing a first differentiation waveform FDPTG (velocity waveform)
FIG. 8C is a waveform diagram showing a second differentiation waveform SDPTG (acceleration waveform).

FIG. 8A shows the original pulse waveform PTG from which the body movement waveform has been removed, FIG. 8B shows the first differentiation waveform FDPTG (velocity waveform), and FIG. 8C shows a second differentiation waveform SDPTG (acceleration waveform). The ejection duration ED may be measured from the first differentiation waveform FDPTG shown in FIG. 8B. As shown in FIG. 8C, more definite inflection points a to e corresponding to the inflection points P0 to P4 shown in FIG. 1 appear in the second differentiation waveform SDPTG. In the second differentiation waveform SDPTG, a time interval between the inflection points a and e corresponds to the ejection duration ED from the rise of the pulse wave to the dicrotic notch. Therefore, the ejection duration calculation section 90 may measure the ejection duration ED from the second differentiation waveform SDPTG. The diastolic time calculation section 91 may measure the diastolic time DT from the difference between one cycle in the second differentiation waveform SDPTG and the ejection duration ED.

Figure 9:
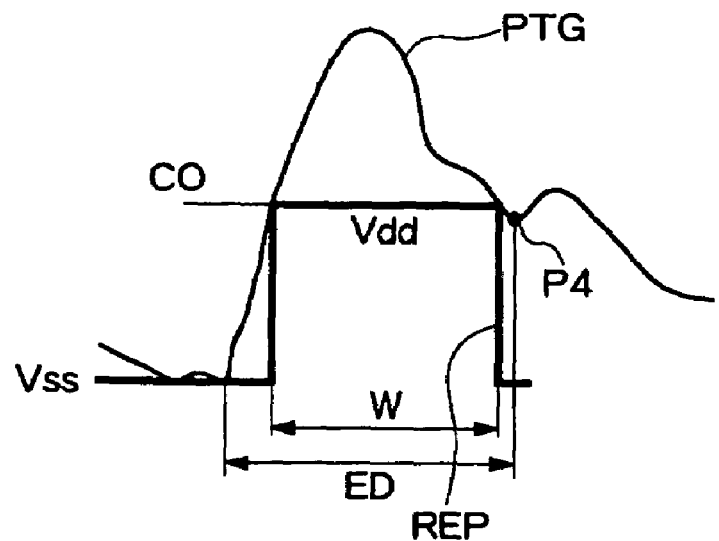
FIG. 9 is a characteristic diagram showing a rectangular wave having a correlation with ejection duration which is generated by comparing a pulse wave with a comparative value by using a comparator.

Second Configuration Example of Ejection Duration Measurement Section or Diastolic Time Measurement Section As shown in FIG. 9, the ejection duration calculation section 90 and the diastolic time calculation section 91 may include a comparator in which a comparative value CO is set near the wave height of the dicrotic notch P4 of the pulse wave PTG from which the body movement waveform has been removed. Output from the comparator is a rectangular wave REP shown in FIG. 9. FIG. 9 shows the rectangular wave REP in the pulse wave PTG for convenience of illustration. A high level of the rectangular wave is at a first power supply potential Vdd of the comparator, and a low level of the rectangular wave is at a second power supply potential Vss.

The pulse width W of the rectangular wave has a correlation with the ejection duration ED from the point P0 to the dicrotic notch P4. Therefore, a time interval corresponding to the pulse width W of the rectangular wave may be taken as the ejection duration ED. The ejection duration change detection section 100 detects whether or not the exercise load intensity exceeds the lactate threshold LT shown in FIG. 2 by detecting the change in the ejection duration ED. The diastolic time calculation section 91 calculates the diastolic time DT by subtracting the ejection duration ED obtained by using the comparator shown in FIG. 9 from one cycle of the pulse wave or the heartbeat calculated by using another method.

Figure 10:
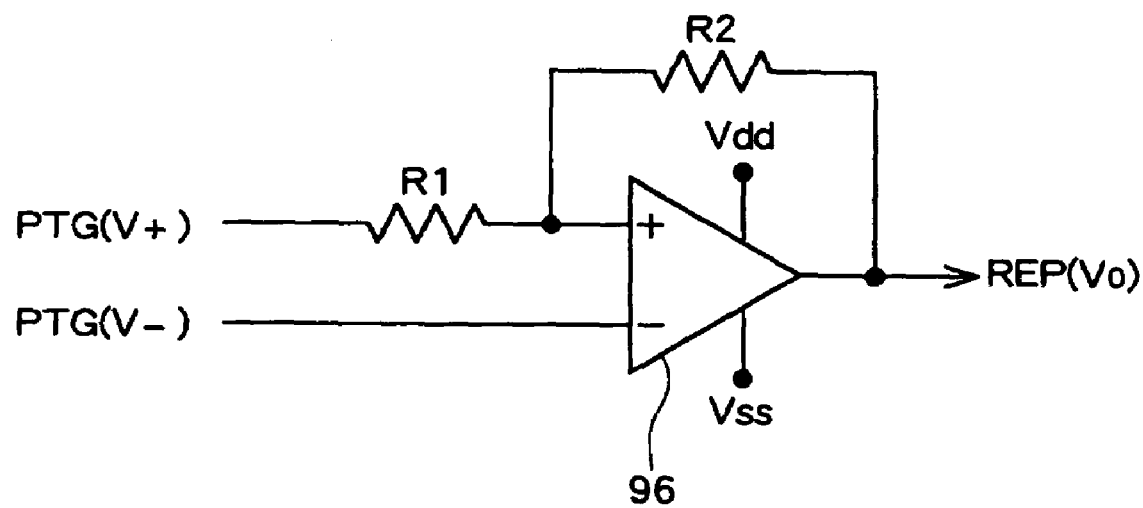
FIG. 10 is a circuit diagram of a comparator with hysteresis which generates the rectangular wave shown in FIG. 9 from a pulse wave.

The comparator is preferably a comparator 96 with hysteresis shown in FIG. 10. The comparator 96 with hysteresis is positively fed back by connecting a feedback resistor R2 with a positive (+) input terminal.

A voltage input to the positive input terminal is expressed by $(V_0 - V_+) \times R_1/(R_1 + R_2) + V_+$. The output voltage $V_0$ is always saturated at one of the first and second power supply potentials Vdd and Vss for driving the comparator 96.

Therefore, $(V_0 - V_+)$ is always greater than 0, and a voltage input to the positive input terminal is always greater than the voltage level $V_+$ of the pulse wave PTG. The number of apparent positive input voltages increases by the positive feedback effect. Therefore, if the output voltage $V_0$ is saturated at either Vdd or Vss, the output voltage is not easily inverted even if the input is changed. In the case where the output voltage $V_0$ is saturated at Vdd, the output is not immediately inverted even if the voltage $V_+$ of the pulse wave PTG becomes lower than the voltage V. of the reference value CO. Therefore, since the rectangular wave REP does not easily rise after the rectangular wave REP falls near the dicrotic notch P4 in FIG. 9, the rectangular wave REP can be generated securely.

Modification of Exercise Load Intensity Evaluation Device

Since the ejection duration ED is almost constant if the exercise load intensity does not reach the lactate threshold LT shown in FIG. 2, the dicrotic notch P4 in the pulse waveform MH2 or MH3 shown in FIG. 1 appears almost in a constant frequency band. Therefore, a frequency of interest is set in advance in the frequency band which reflects the dicrotic notch P4. It is determined that the ejection duration ED is changed if the frequency spectrum of the frequency band of interest exceeds an allowable value on the frequency axis. Since the ejection duration ED decreases if the exercise load intensity exceeds the lactate threshold LT, the frequency spectrum which reflects the dicrotic notch P4 should shift to the high frequency side. Therefore, the change in the ejection duration ED can be detected by detecting the shift of the frequency spectrum.

Since the diastolic time DT is almost constant after the exercise load intensity reaches the lactate threshold LT shown in FIG. 16, the dicrotic notch P4 in the pulse waveform MH2 or MH3 shown in FIG. 1 appears almost in a constant frequency band. Therefore, a frequency of interest is set in advance in the frequency band which reflects the dicrotic notch P4. It is determined that the diastolic time DT is changed if the frequency spectrum of the frequency band of interest exceeds an allowable value on the frequency axis. Since the diastolic time DT increases if the exercise load intensity exceeds the lactate threshold LT, the frequency spectrum which reflects the dicrotic notch P4 should shift to the low frequency side. Therefore, the change in the diastolic time DT can be detected by detecting the shift of the frequency spectrum.

Figure 11:
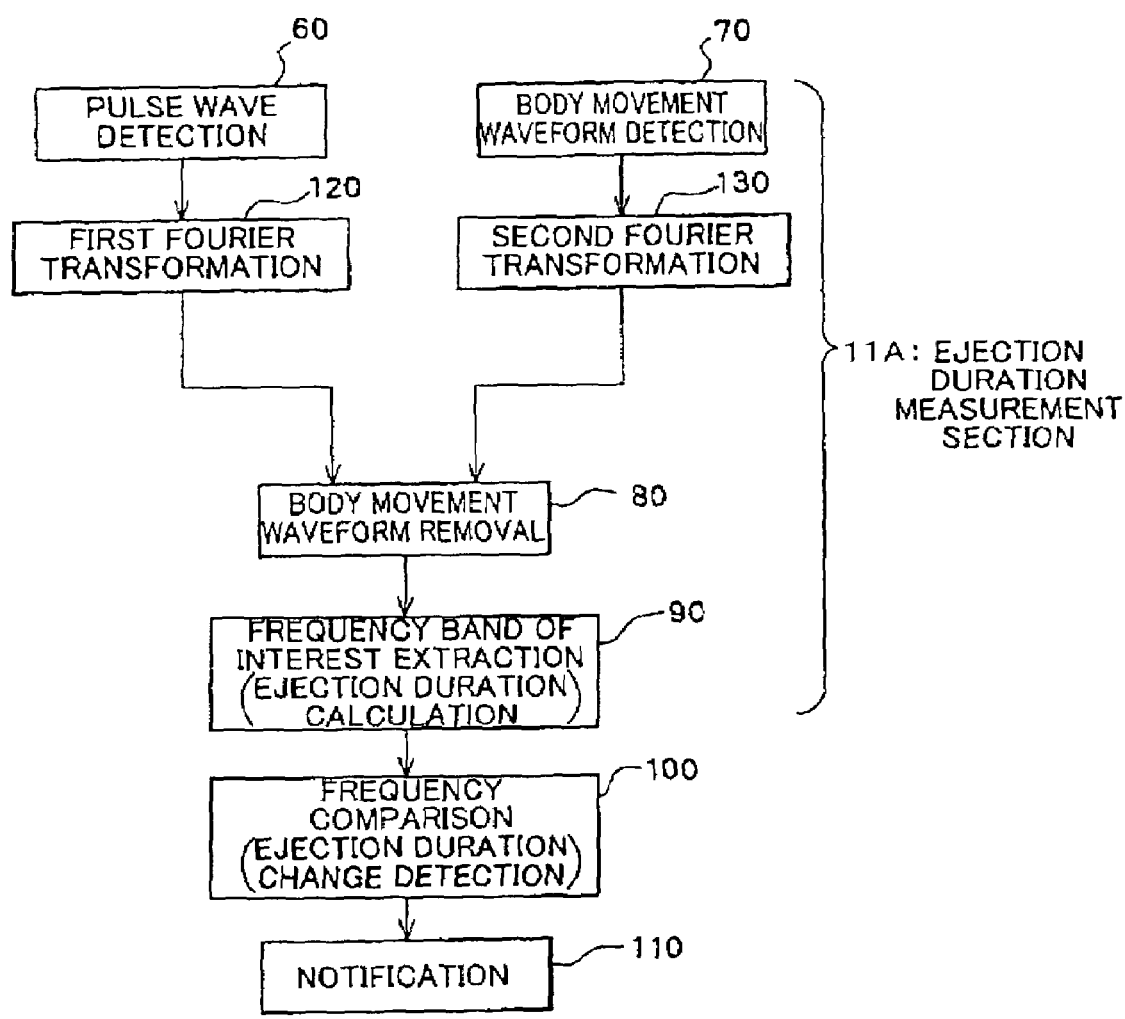
FIG. 11 is a block diagram showing a modification of an exercise load intensity evaluation device which monitors a frequency spectrum corresponding to ejection duration.
Figure 18:
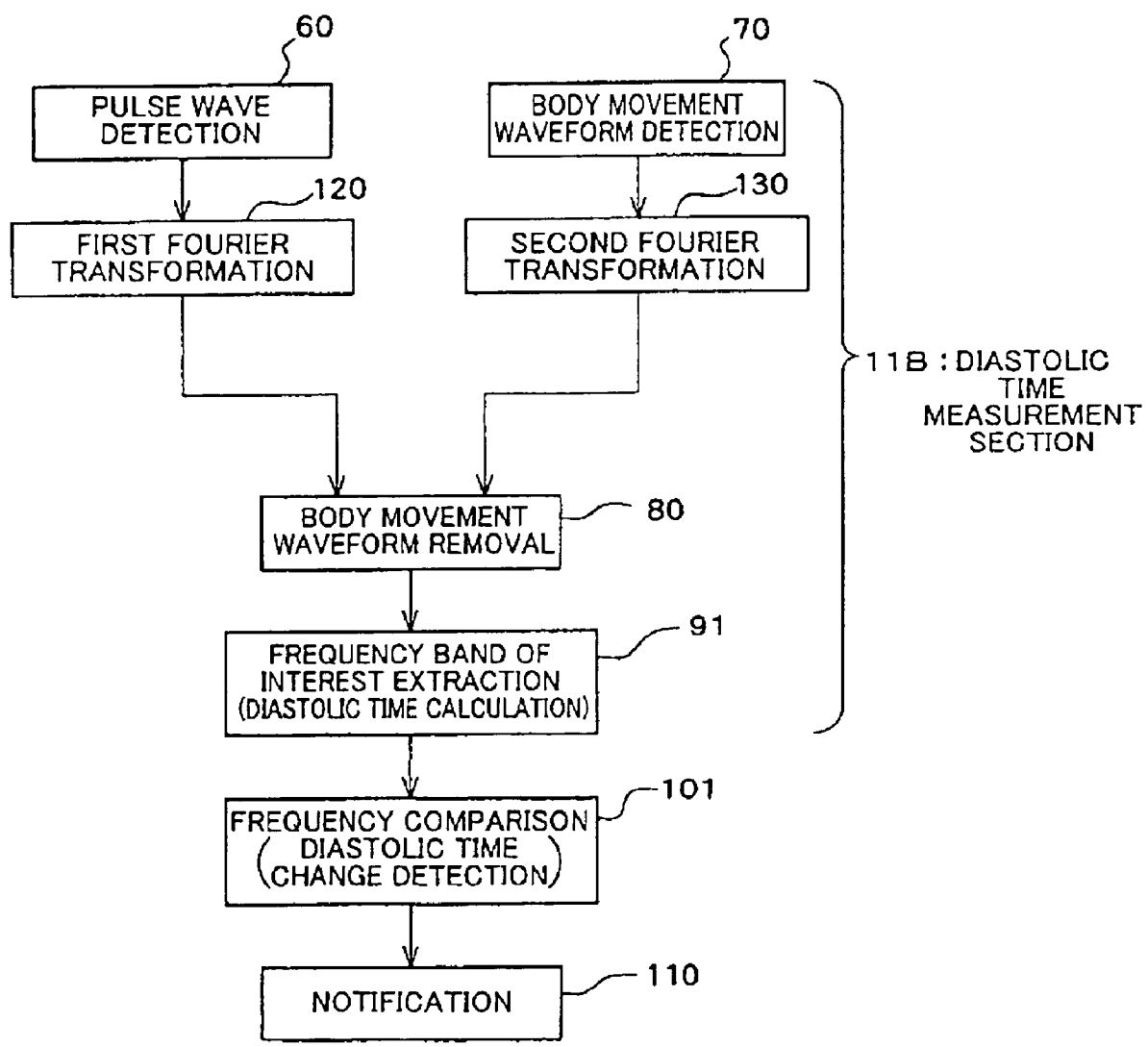
FIG. 18 is a block diagram showing a modification of an exercise load intensity evaluation device which monitors a frequency spectrum corresponding to diastolic time.

As shown in FIGS. 11 and 18, the exercise load intensity evaluation device includes a first Fourier transformation section 120 which transforms the pulse wave detected by the pulse wave detection section 60, and a second Fourier transformation section 130 which transforms the body movement waveform detected by the body movement waveform detection section 70. The body movement waveform removal section 80 subtracts the frequency spectra at the same frequency output from the first and second Fourier transformation sections 120 and 130 to remove the body movement waveform. The ejection duration calculation section 90 and the diastolic time calculation section 91 are formed by using frequency band of interest extraction sections. The frequency band of interest extraction sections 90 and 91 extract the frequency spectrum in the frequency band of interest which reflects the ejection duration ED of a subject from various frequency spectra output from the body movement waveform removal section 80. The ejection duration measurement section 11A or the diastolic time measurement section 11B is formed by the above-described configuration. The ejection duration change detection section 100 and the diastolic time change detection section 101 are formed by frequency comparison sections, and compare the frequency of the latest frequency spectrum in the frequency band of interest with the last reference frequency extracted, for example. If the latest frequency spectrum exceeds the allowable value toward the high frequency side on the frequency axis in comparison with the reference frequency, it is determined that the ejection duration ED or the diastolic time DT is changed. In this case, the heart rate can be calculated by setting the frequency spectrum in the frequency band of interest which reflects the dicrotic notch P4 in the pulse waveform MH2 or MH3 shown in FIG. 1, and extracting the frequency spectrum in the frequency band of interest which reflects one cycle of the pulse wave.

Figure 12:
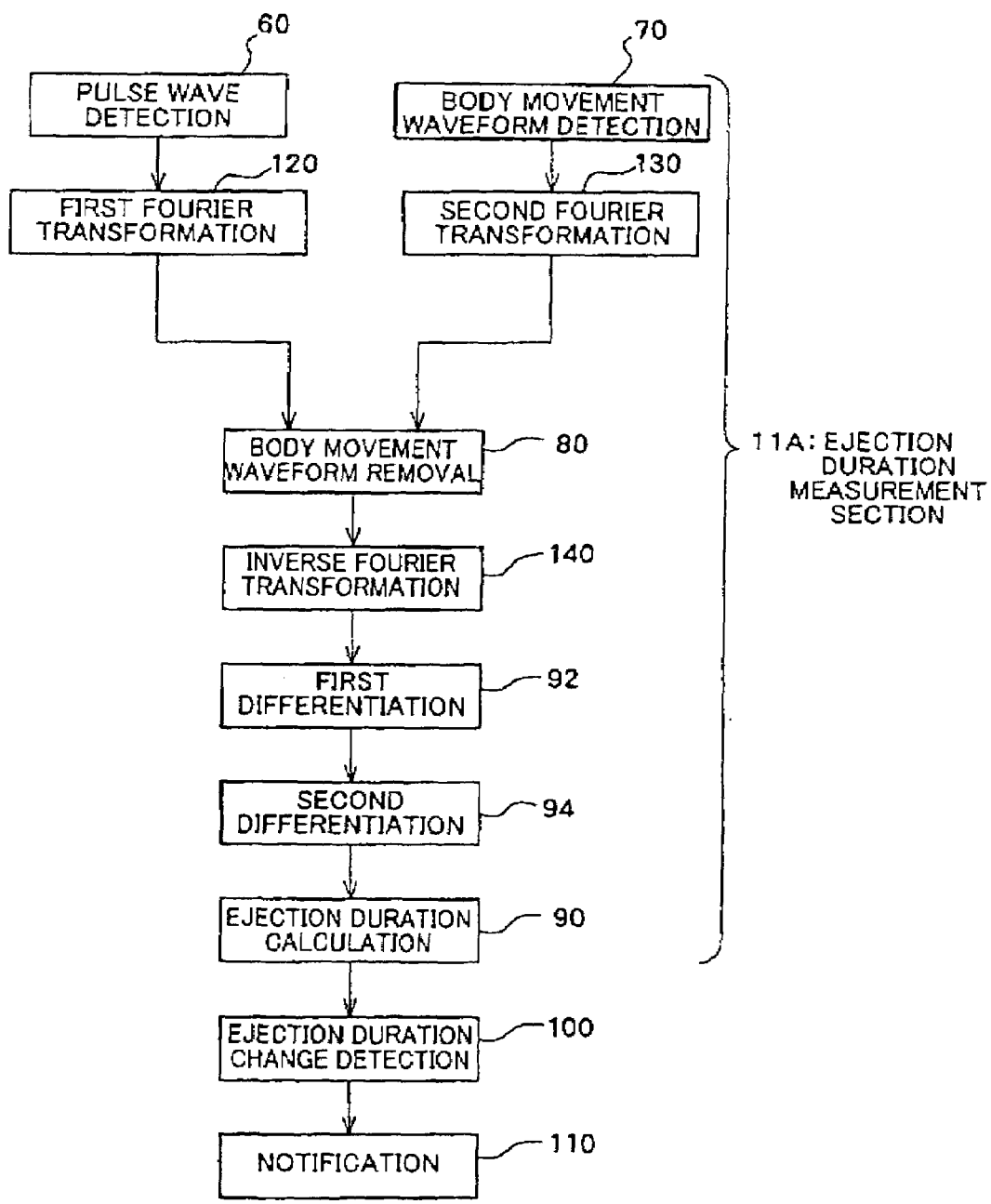
FIG. 12 is a block diagram showing a modification of an exercise load intensity evaluation device which removes body movement based on a frequency spectrum and measures ejection duration from a feature of a second differentiation pulse waveform.
Figure 19:
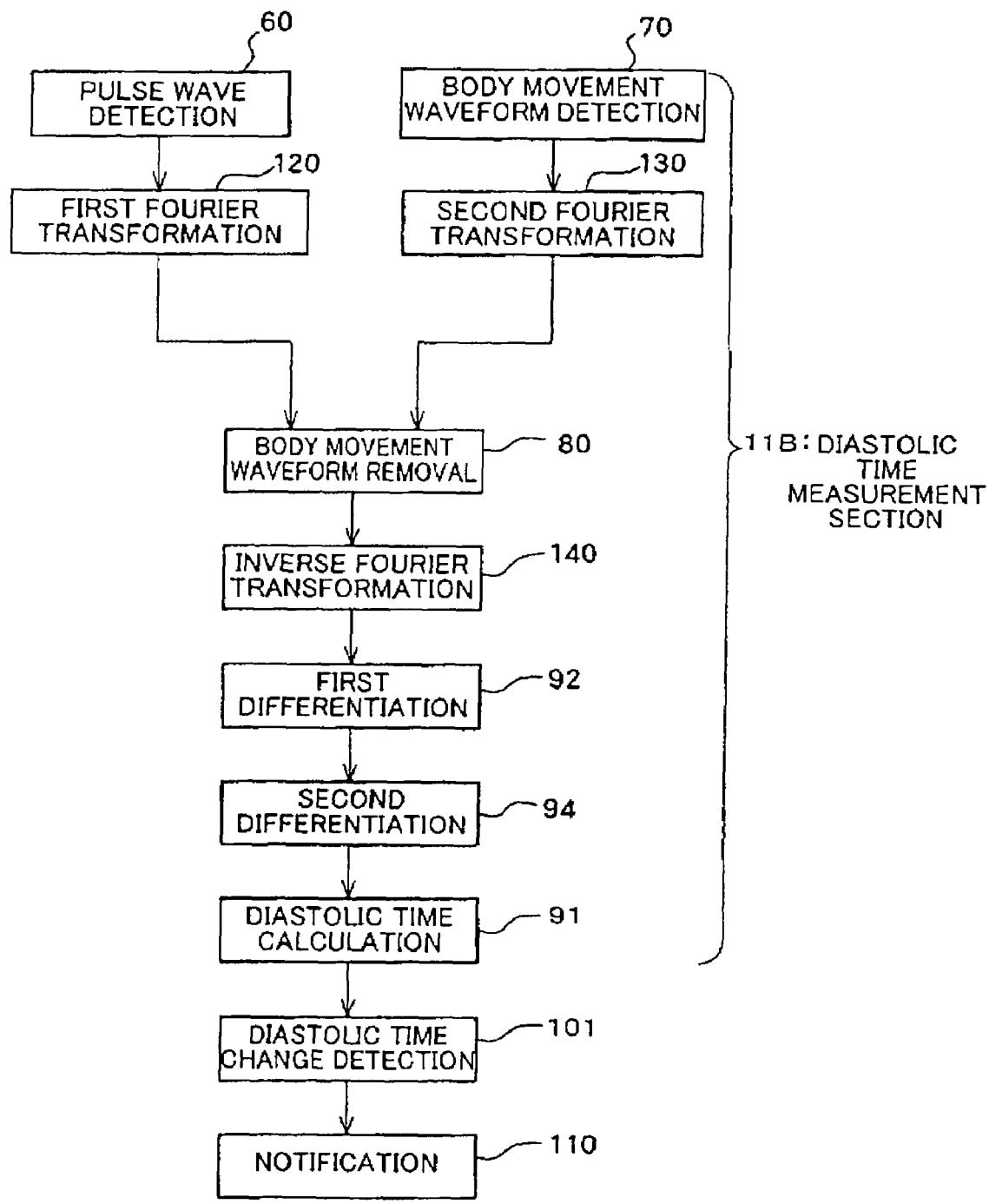
FIG. 19 is a block diagram showing a modification of an exercise load intensity evaluation device which removes body movement based on a frequency spectrum and measures diastolic time from a feature of a second differentiation pulse waveform.

FIGS. 12 and 19 show other modifications of the exercise load intensity evaluation device. The exercise load intensity evaluation devices shown in FIGS. 12 and 19 have the same configuration as those shown in FIGS. 11 and 18 from the pulse wave detection section 60 to the body movement waveform removal section 80. The exercise load intensity evaluation devices shown in FIGS. 12 and 19 include an inverse Fourier transformation section 140 which converts the output from the body movement waveform removal section 80 into an analog waveform by performing an inverse Fourier transformation.

The configuration subsequent to the inverse Fourier transformation section 140 is the same as those shown in FIGS. 4 and 17. The first and second differentiation sections 92 and 94 are provided as the ejection duration calculation section 90 shown in FIG. 4 and the diastolic time calculation section 91 shown in FIG. 17. The ejection duration measurement section 11A is formed by the components from the pulse wave detection section 60 to the ejection duration calculation section 90 shown in FIG. 12. The diastolic time measurement section 11B is formed by the components from the pulse wave detection section 60 to the diastolic time calculation section 91 shown in FIG. 19.

According to the configurations shown in FIGS. 12 and 19, the body movement waveform included in the pulse wave is distinguished by the frequency band and removed from the pulse wave. The ejection duration ED and the diastolic time DT are measured from the feature of the first differentiation waveform or the second differentiation waveform.

Figure 13:
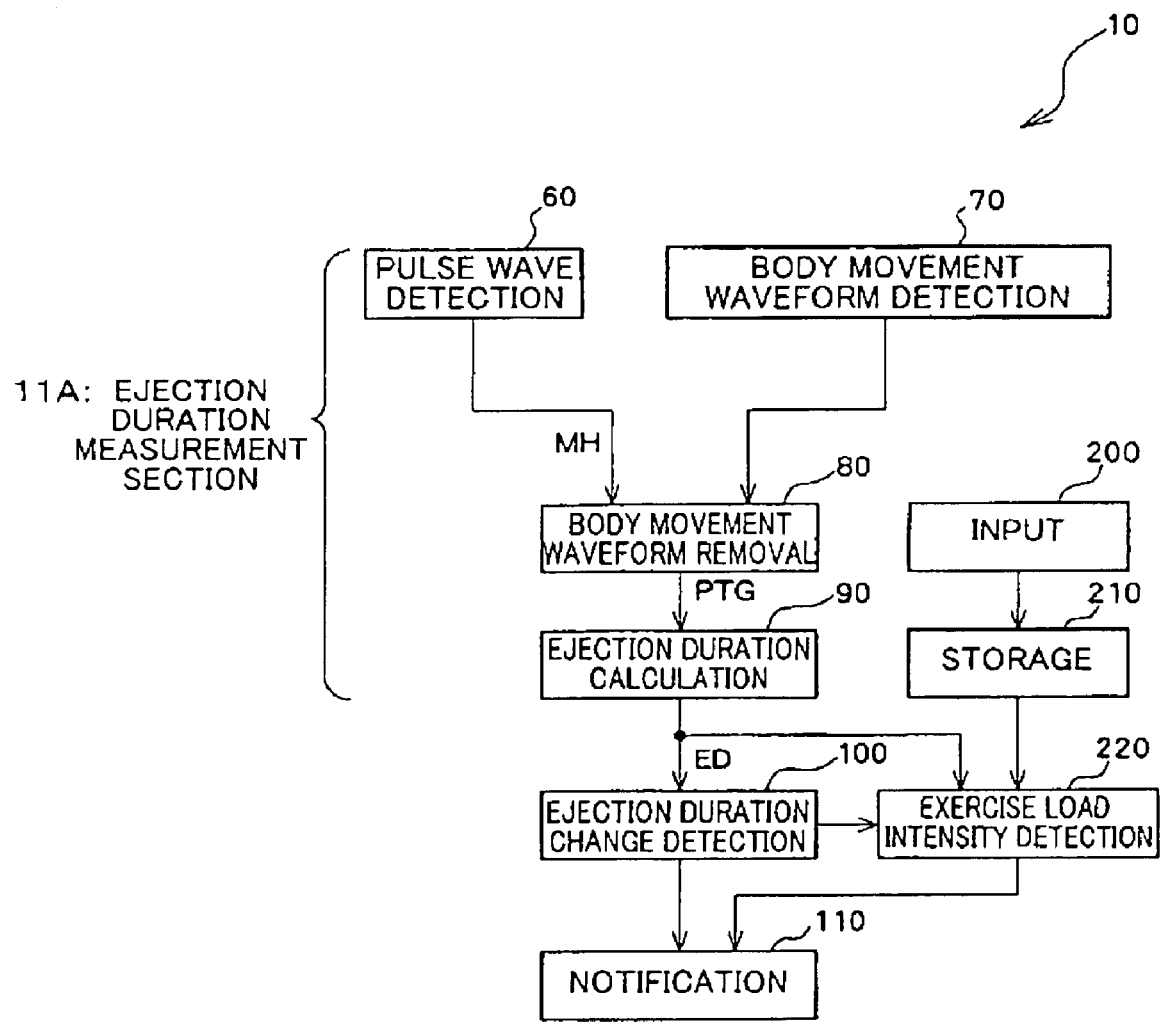
FIG. 13 is a block diagram showing a modification in which exercise load intensity is detected from ejection duration measured during exercise based on correlation data between ejection duration and exercise load intensity measured in advance.
Figure 20:
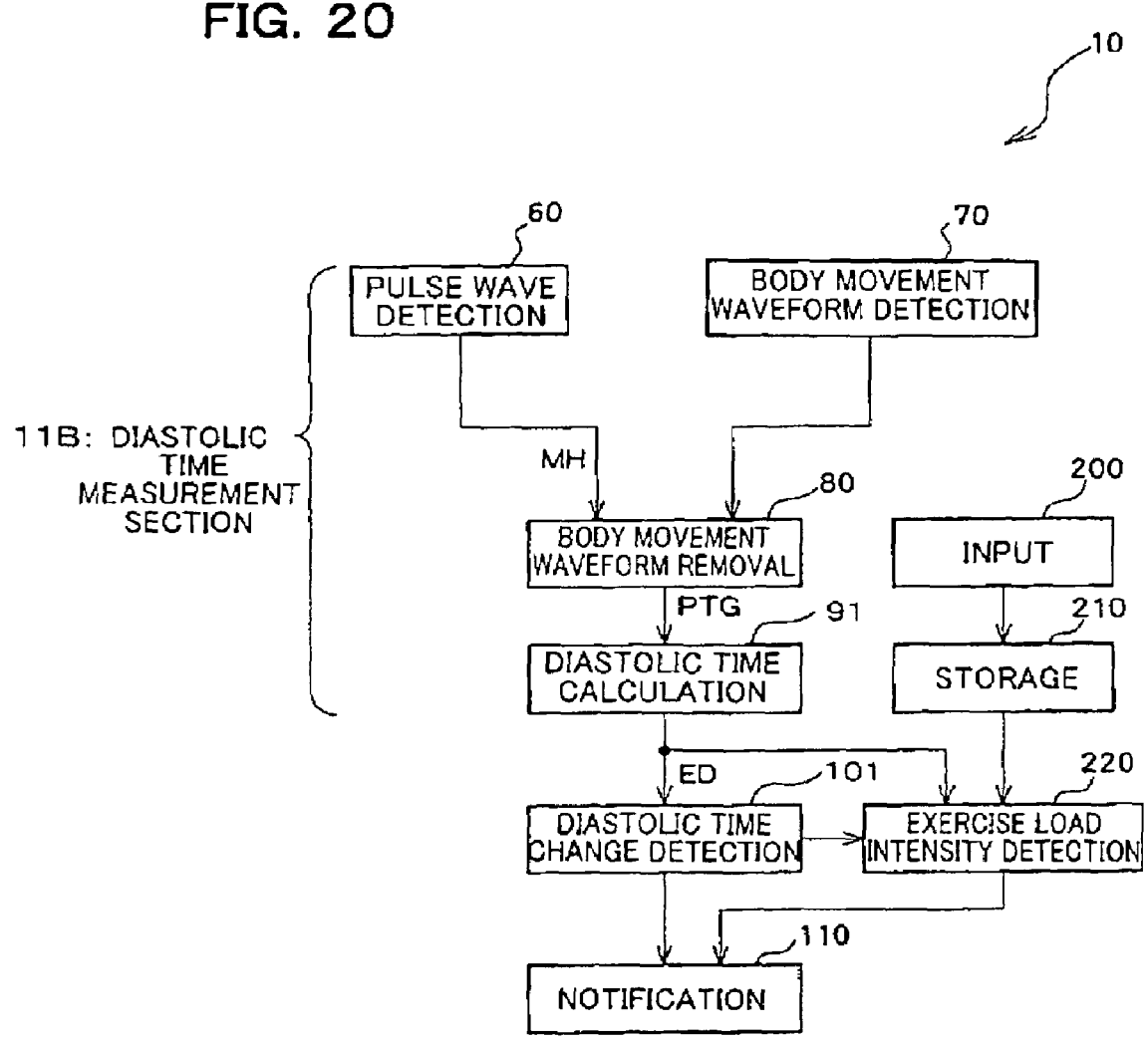
FIG. 20 is a block diagram showing a modification in which exercise load intensity is detected from diastolic time measured during exercise based on correlation data between diastolic time and exercise load intensity which have been measured in advance.

FIGS. 13 and 20 show still other modifications of the exercise load intensity evaluation device.

The correlation data between the exercise load intensity and the ejection duration or the heart rate corresponding to the ejection duration of a subject shown in FIG. 2 may be calculated in advance. Specifically, the ejection duration or the heart rate corresponding to the ejection duration at each exercise load intensity is calculated in advance by performing an exercise test in which a subject is allowed to walk or run while changing the degree of exercise load intensity. The correlation data between the exercise load intensity and the diastolic time or the heart rate corresponding to the diastolic time of a subject shown in FIG. 16 may be calculated in advance. Specifically, the diastolic time or the heart rate corresponding to the diastolic time at each exercise load intensity is calculated in advance by performing an exercise test in which a subject is allowed to walk or run while changing the degree of exercise load intensity. As shown in FIGS. 13 and 20, the correlation data is stored in a storage section 210 through an input section 200, for example. In FIGS. 13 and 20, an exercise load intensity detection section 220 is further provided. The exercise load intensity detection section 220 shown in FIG. 13 reads the exercise load intensity corresponding to the ejection duration ED output from the ejection duration calculation section 90 or the exercise load intensity corresponding to the heart rate corresponding to the ejection duration from the storage section 210, and outputs the exercise load intensity to the notification section 110. The exercise load intensity detection section 220 shown in FIG. 20 reads the exercise load intensity corresponding to the diastolic time DT output from the diastolic time calculation section 91 or the exercise load intensity corresponding to the heart rate corresponding to the diastolic time from the storage section 210, and outputs the exercise load intensity to the notification section 110. This enables the subject to recognize the current exercise load intensity as power (watt) or the heart rate (beat/min).

As shown in FIG. 2, the ejection duration is constant or decreases to only a small extent until the exercise load intensity exceeds the lactate threshold LT. Therefore, it is difficult to detect the exercise load intensity in the aerobic exercise stage in which the change in the ejection duration is small, and the subject rarely demands to know the exercise load intensity in the aerobic exercise stage. In the present embodiment, the exercise load intensity detection section 220 may detect the exercise load intensity when the ejection duration is substantially changed in the ejection duration change detection section 100, specifically, when entering the exercise stage exceeding the lactate threshold LT. As shown in FIG. 13, a signal output from the ejection duration change detection section 100 is input to the exercise load intensity detection section 220. In the present embodiment, a time interval of one cycle of the heartbeat for calculating the heart rate is output when the ejection duration is substantially changed in the ejection duration change detection section 100.

As shown in FIG. 16, the diastolic time DT is substantially constant or decreases to only a small extent after the exercise load intensity exceeds the lactate threshold LT. Therefore, it is difficult to detect the exercise load intensity in the anaerobic exercise stage in which the change in the diastolic time is small, and the subject rarely demands to know the exercise load intensity in the anaerobic exercise stage. In the present embodiment, the exercise load intensity detection section 220 may detect the exercise load intensity when the diastolic time is substantially constant or decreases to only a small extent in the diastolic time change detection section 101, specifically, when entering the exercise stage exceeding the lactate threshold LT. As shown in FIG. 20, a signal output from the diastolic time change detection section 101 is input to the exercise load intensity detection section 220. In the present embodiment, a time interval of one cycle of the heartbeat for calculating the heart rate is output when the diastolic time is not substantially changed in the diastolic time change detection section 101.

Exercise Equipment

Exercise equipment may be formed by incorporating the above-described exercise load intensity evaluation device. In the present embodiment, the upper limit and the lower limit of the exercise load intensity may be set by using the heart rate based on the heart rate which can be output from the ejection duration change detection section 100 when the ejection duration ED is substantially changed in the ejection duration change detection section 100, specifically, when the exercise load intensity approaches the lactate threshold LT. The upper limit and the lower limit of the exercise load intensity may be set by using the heart rate based on the heart rate which can be output from the diastolic time change detection section 101 when the diastolic time DT is not substantially changed in the diastolic time change detection section 101, specifically, when the exercise load intensity approaches the lactate threshold LT. FIGS. 5A to 5C illustrate the wristwatch type exercise load intensity evaluation device. However, in the case of applying the present invention to exercise equipment, only the detection section which detects the pulse wave or electrocardiogram of a subject may be attached to the subject, and the other components may be installed on the exercise equipment.

Figure 14:
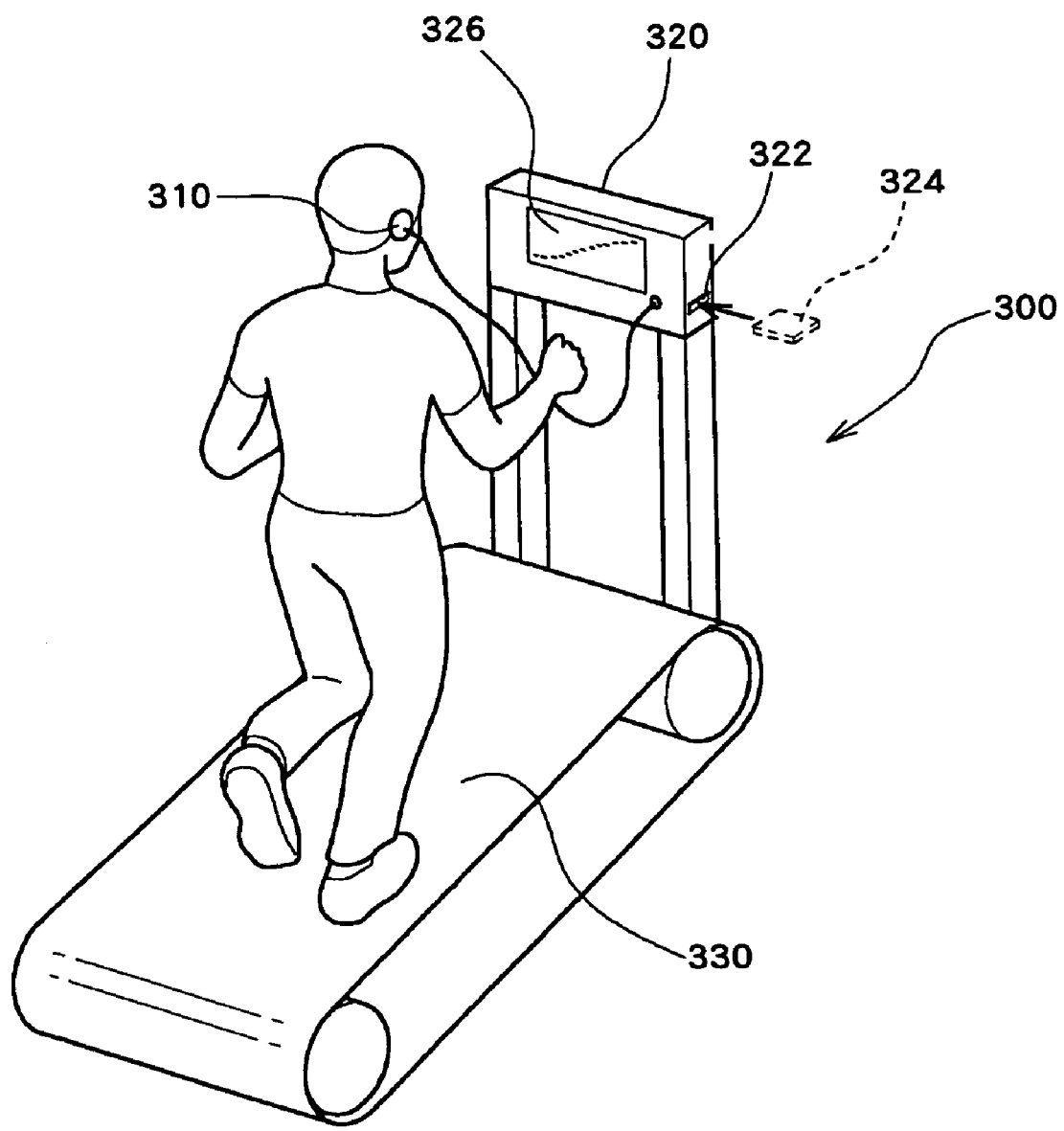
FIG. 14 is a diagram schematically showing a running/walking machine which is an example of exercise equipment of the present invention.

FIG. 14 shows a running/walking machine 300. A pulse wave detection section 310 which detects a pulse wave from the ear of a subject is connected with a body section 320. The pulse wave may be detected from a part other than the earlobe such as the finger as in the above embodiment or the wrist.

In the running/walking machine 300 shown in FIG. 14, the velocity of a belt 330 as a load output section is variable based under control by the body section 320. A storage medium 324 is removably inserted into a storage medium insertion section 322 of the body section 320. An exercise menu for the subject is recorded on the storage medium 324, and the exercise menu can be displayed in an output section provided to the body section 320 such as a display section 326. The display section 326 may also be used as a notification section which notifies the subject when the exercise load intensity enters the exercise stage exceeding the lactate threshold.

The exercise load intensity and the cardiac ejection duration (or diastolic time) may be measured in advance for each subject by using the above-described exercise load intensity evaluation device, and a safe and effective exercise menu may be set for each subject. The safe and effective exercise menu is set in a predetermined exercise load intensity range based on the lactate threshold LT calculated in advance for each subject from the correlation between the exercise load intensity and the ejection duration (or diastolic time). The exercise load intensity range may be set near the lactate threshold LT for a person suffering from heart disease and a healthy person, for example. The exercise load intensity range may be set in a range exceeding the lactate threshold LT for an athlete, for example. This enables an extreme exercise situation such as a last spurt in the actual game to be reproduced by using the exercise equipment, whereby effective training can be achieved.

Figure 15:
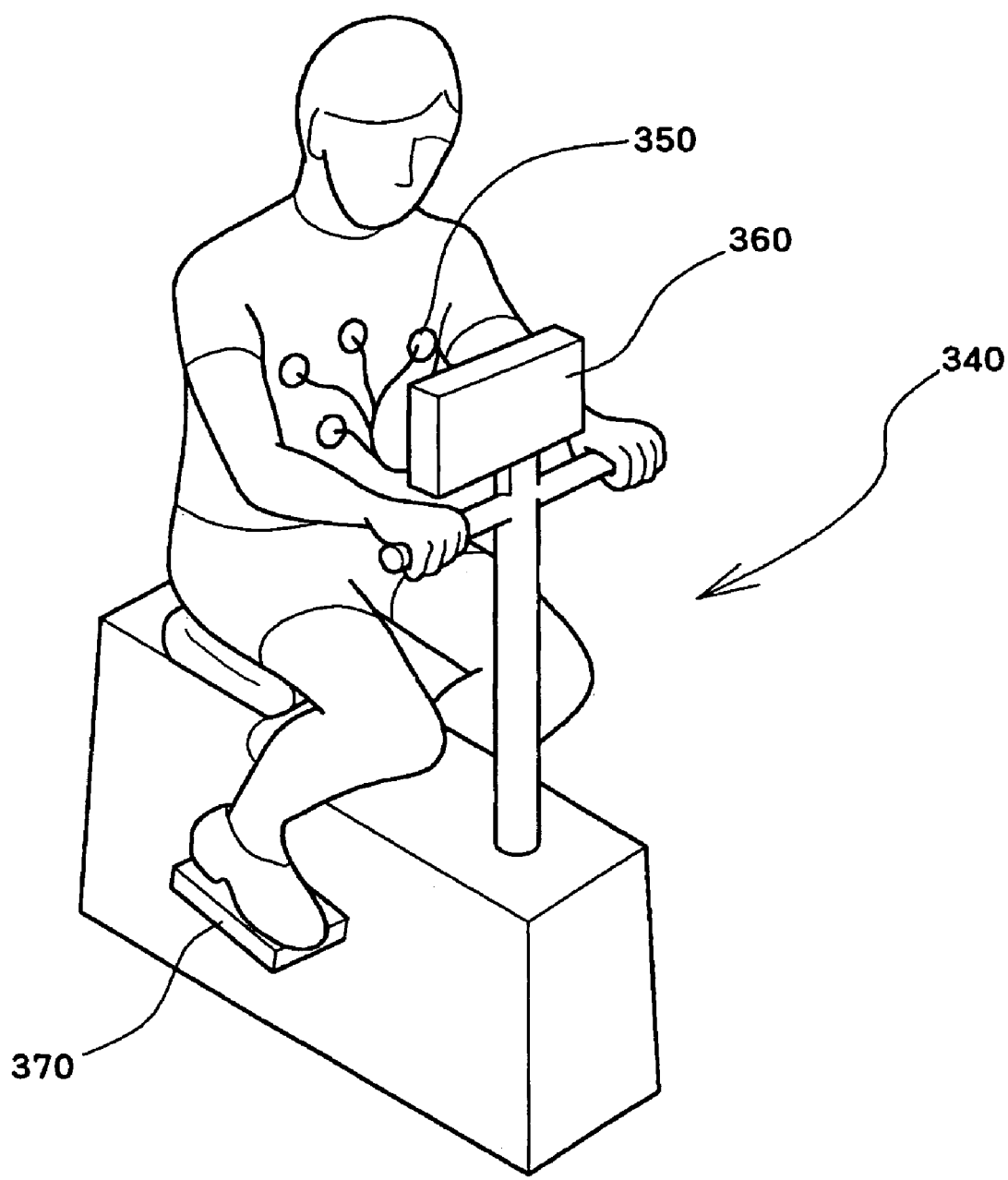
FIG. 15 is a schematic explanatory diagram showing a pedal machine which is another example of exercise equipment of the present invention.

FIG. 15 illustrates the case where the present invention is applied to a pedal machine 340. In this example, an electrocardiogram detection section 350 which is attached to the chest of a subject is connected with a body section 360. The load output section of the pedal machine 340 is a pedal 370. The load necessary for rotating the pedal 370 is variable based under control by the body section 360. The electrocardiogram detection section 350 detects the electrocardiogram waveform SW shown in FIG. 1. An ejection duration measurement section which measures the time Q-T from the electrocardiogram waveform SW shown in FIG. 1 as the ejection duration ED is provided inside the body section 360. A diastolic time measurement section may be provided inside the body section 360 instead of the ejection duration measurement section. The diastolic time measurement section detects the time R–R shown in FIG. 1 as one cycle of the heartbeat and the time Q-T as the ejection duration ED from the electrocardiogram waveform SW, and measures the diastolic time DT from the difference between the time R—R and the time Q-T. The recording media insertion section 322, the recording medium 324, and the display section 326 shown in FIG. 14 are also provided (not shown in FIG. 15).

The present invention is not limited to the above-described embodiment. Various modifications and variations are possible within the spirit and scope of the present invention.

The ratio of the ejection duration ED or the diastolic time DT to one cycle of the heartbeat (time R—R in the electrocardiogram waveform SW or time P0—P0 in the pulse waveform MH2 or MH3 shown in FIG. 1) (hereinafter referred to as "normalized ejection duration" or "normalized diastolic time") may be used as an index instead of the ejection duration in the above embodiment, and whether or not the exercise load intensity has reached the lactate threshold LT may be detected based on the normalized ejection duration or the normalized diastolic time.

One cycle of the heartbeat decreases at a constant rate as the exercise load intensity increases irrespective of the lactate threshold LT. On the contrary, the rate of change in the ejection duration ED differs across the lactate threshold LT as shown in FIG. 2. Therefore, the normalized ejection duration decreases in proportion to the rate of decrease in one cycle of the heartbeat as the exercise load intensity increases until the exercise load intensity reaches the lactate threshold LT, and the rate of decrease in the normalized ejection duration significantly decreases after the exercise load intensity has reached the lactate threshold LT. This is because both one cycle of the heartbeat and the ejection duration decrease after the exercise load intensity reaches the lactate threshold LT. A subject can be notified that the exercise load intensity has reached the lactate threshold LT or notified of the exercise load intensity during exercise from the normalized ejection duration in the above embodiment.

The normalized diastolic time is described below. One cycle of the heartbeat decreases at a constant rate as the exercise load intensity increases irrespective of the lactate threshold LT. On the contrary, the rate of change in the diastolic time DT differs across the lactate threshold LT, as shown in FIG. 16.

Figure 21:
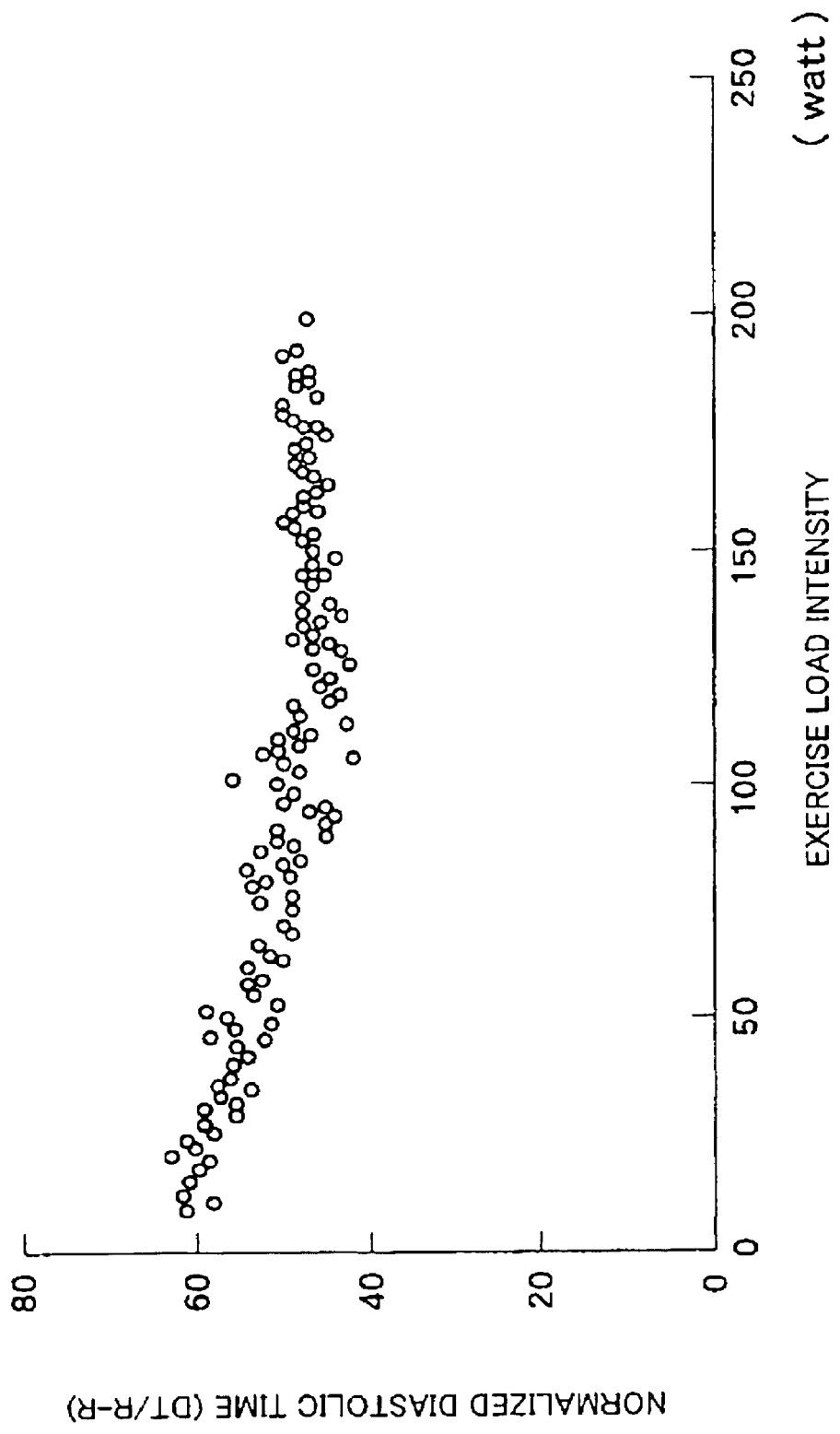
FIG. 21 is a characteristic diagram showing the relation between exercise load intensity and normalized diastolic time.

FIG. 21 is a graph in which the relation between the exercise load intensity and the normalized diastolic time is plotted. The horizontal axis indicates the exercise load intensity and the vertical axis indicates the diastolic time DT. The normalized diastolic time is plotted at each exercise load intensity. The exercise load intensity corresponding to the lactate threshold LT is about 100 watts. The normalized diastolic time decreases as the exercise load intensity increases in the range in which the exercise load intensity does not exceed the lactate threshold LT. The normalized diastolic time is almost constant independent of the exercise load intensity in the range in which the exercise load intensity exceeds the lactate threshold LT.

Figure 22:
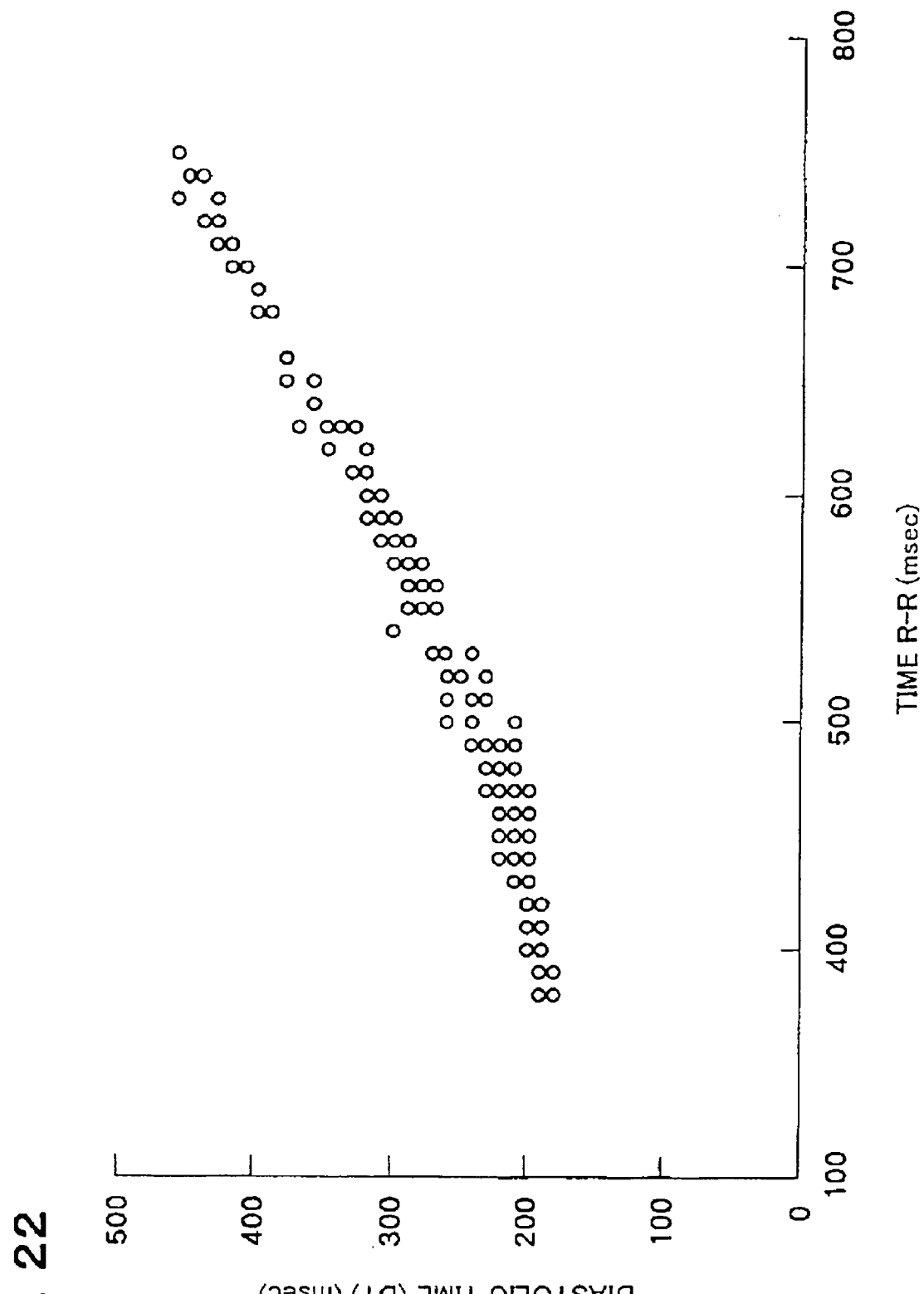
FIG. 22 is a characteristic diagram showing the relation between a cardiac cycle and normalized diastolic time.

FIG. 22 shows a graph in which the time R—R shown in FIG. 16 and the diastolic time DT are plotted at each exercise load intensity. The horizontal axis indicates the time R—R and the vertical axis indicates the diastolic time DT. The exercise load intensity corresponding to the lactate threshold LT shown in FIG. 16 is about 101 watts. The time R—R corresponding to exercise load intensity of 101 watts is about 500 msec. In FIG. 22, the normalized diastolic time decreases as the exercise load intensity increases (toward the left direction along the horizontal axis) in the range in which the time R—R exceeds 500 msec (range in which the exercise load intensity does not exceed the lactate threshold LT). The normalized diastolic time is almost constant independent of the exercise load intensity in the range in which the time R—R does not exceed 500 msec (range in which the exercise load intensity exceeds the lactate threshold LT).

The diastolic time is substantially constant even if the exercise load intensity increases until the exercise load intensity reaches the lactate threshold LT. However, the rate of decrease in the diastolic time is almost in proportion to the rate of decrease in one cycle of the heartbeat after the exercise load intensity has reached the lactate threshold LT. A subject can be notified that the exercise load intensity has reached the lactate threshold LT or of the exercise load intensity during exercise from the diastolic time in the above embodiment.

What is claimed is:

1. An exercise load intensity evaluation device comprising:
   an ejection duration measurement section which noninvasively measures cardiac ejection duration of a subject during exercise; and
   an ejection duration change detection section which detects a change in the ejection duration which is measured at each measurement time by the ejection duration measurement section and is input to the ejection duration change detection section.

2. The exercise load intensity evaluation device as defined in claim 1, further comprising:
   an exercise load intensity measurement section which measures exercise load intensity of the subject,
   wherein the ejection duration change detection section detects a change in the ejection duration corresponding to different degrees of exercise load intensity based on output from the exercise load intensity measurement section.

3. The exercise load intensity evaluation device as defined in claim 1,
   wherein the ejection duration measurement section includes an electrocardiogram measurement section which measures an electrocardiogram of the subject during exercise, and measures the ejection duration from a feature of the electrocardiogram which reflects the cardiac ejection duration.

4. The exercise load intensity evaluation device as defined in claim 1,
   wherein the ejection duration measurement section includes a pulse wave detection section which is attached to the subject during exercise and noninvasively detects a peripheral pulse wave, and measures the ejection duration from a feature of the pulse wave which reflects the cardiac ejection duration.

5. The exercise load intensity evaluation device as defined in claim 1,
   wherein the ejection duration measurement section includes:
   a pulse wave detection section which is attached to the subject during exercise and noninvasively detects a peripheral pulse wave; and
   an ejection duration correction section which corrects the cardiac ejection duration based on output from the pulse wave detection section.

6. The exercise load intensity evaluation device as defined in claim 4,
   wherein the ejection duration measurement section further includes:
   a body movement waveform detection section which detects a body movement waveform according to body movement of the subject during exercise; and
   a body movement waveform removal section which removes the body movement waveform detected by the body movement waveform detection section from the pulse wave detected by the pulse wave detection section, and
   wherein the ejection duration measurement section measures the ejection duration based on the pulse wave from which the body movement waveform has been removed.

7. The exercise load intensity evaluation device as defined in claim 4,
   wherein the ejection duration measurement section measures a time interval from rise of the pulse wave to a dicrotic notch.

8. The exercise load intensity evaluation device as defined in claim 4,
   wherein the ejection duration measurement section includes a first differentiation section which differentiates the pulse wave; and a second differentiation section which differentiates the pulse wave differentiated by the first differentiation section, and measures the ejection duration based on the pulse wave differentiated by the second differentiation section.

9. The exercise load intensity evaluation device as defined in claim 4,
   wherein the ejection duration measurement section includes a comparator which compares a wave height of the pulse wave with a reference value, and measures the ejection duration based on a pulse width of a rectangular wave output from the comparator.

10. The exercise load intensity evaluation device as defined in claim 9,
    wherein the comparator is a comparator with hysteresis and having a positive input terminal which is connected with a feed back resistor.

11. The exercise load intensity evaluation device as defined in claim 4,
    wherein the ejection duration measurement section further includes a Fourier transformation section which transforms the pulse wave detected by the pulse wave detection section,
    wherein the ejection duration measurement section extracts a frequency spectrum which is obtained based on the feature of the pulse wave which reflects the cardiac ejection duration from Fourier transformed frequency spectra, and
    wherein the ejection duration change detection section detects a change in frequency of the frequency spectrum extracted at each measurement time by the ejection duration measurement section.

12. The exercise load intensity evaluation device as defined in claim 6, wherein the ejection duration measurement section further includes:
a first Fourier transformation section which transforms the pulse wave detected by the pulse wave detection section; and
a second Fourier transformation section which transforms the body movement waveform detected by the body movement waveform detection section, and
wherein the body movement waveform removal section subtracts frequency spectra at the same frequency among frequency spectra in each frequency band output from the first and second Fourier transformation sections.

13. The exercise load intensity evaluation device as defined in claim 12,
wherein the ejection duration measurement section extracts a frequency spectrum which is obtained based on the feature of the pulse wave which reflects the cardiac ejection duration from frequency spectra output from the body movement waveform removal section, and
wherein the ejection duration change detection section detects a change in frequency of the frequency spectrum extracted at each measurement time by the ejection duration measurement section.

14. The exercise load intensity evaluation device as defined in claim 12,
wherein the ejection duration measurement section includes an inverse Fourier transformation section which performs inverse Fourier transformation of output from the body movement waveform removal section; a first differentiation section which differentiates the pulse wave which has been inverse-Fourier-transformed; and a second differentiation section which differentiates the pulse wave differentiated by the first differentiation section, and measures the ejection duration based on the pulse wave differentiated by the second differentiation section.

15. The exercise load intensity evaluation device as defined in claim 1, further comprising:
a notification section which notifies the subject when the exercise load intensity exceeds a lactate threshold based on output from the ejection duration change detection section.

16. The exercise load intensity evaluation device as defined in claim 1, further comprising:
a notification section which notifies the subject when the exercise enters anaerobic exercise based on output from the ejection duration change detection section.

17. An exercise load intensity evaluation device comprising:
an ejection duration measurement section which noninvasively measures cardiac ejection duration of a subject during exercise;
a storage section which stores correlation data between the ejection duration or a heart rate corresponding to one cycle of a heartbeat at the ejection duration and exercise load intensity; and
an exercise load intensity detection section which detects the exercise load intensity from the storage section based on the ejection duration measured by the ejection duration measurement section.

18. The exercise load intensity evaluation device as defined in claim 17, further comprising:
an ejection duration change detection section which detects a change in the ejection duration which is measured at each measurement time by the ejection duration measurement section and is input to the ejection duration change detection section,
wherein the exercise load intensity detection section detects the exercise load intensity when the ejection duration change detection section detects that the ejection duration is changed.

19. The exercise load intensity evaluation device as defined in claim 1,
wherein a ratio of the ejection duration to one cycle of a heartbeat is used as an index instead of the ejection duration.

20. The exercise load intensity evaluation device as defined in claim 1,
wherein the ejection duration change detection section outputs one cycle of a heartbeat when the ejection duration changes.

21. The exercise load intensity evaluation device as defined in claim 15,
wherein the notification section includes a storage section which stores the ejection duration exceeding a safe exercise range, and notifies the subject that the exercise load intensity is out of the safe exercise range when the measured ejection duration is smaller than the ejection duration stored in the storage section.

22. Exercise equipment comprising the exercise load intensity evaluation device as defined in claim 1.

23. The exercise equipment as defined in claim 22,
wherein a range of the exercise load intensity is set as a range of a heart rate based on one cycle of a heartbeat output from the ejection duration change detection section.

24. The exercise equipment as defined in claim 22, further comprising:
an output section which outputs exercise menus of different degrees of exercise load intensity.

25. The exercise equipment as defined in claim 22, further comprising:
a load output section which outputs exercise load which is applied to the subject according to an exercise menu at different degrees of exercise load intensity.

26. The exercise equipment as defined in claim 24,
wherein each of the exercise menus is set in a predetermined exercise load intensity range based on a lactate threshold calculated for the subject from a correlation between the exercise load intensity and the ejection duration.

27. The exercise equipment as defined in claim 26, further comprising:
a storage medium which stores the exercise menus and is removable from the exercise equipment.

28. An exercise load intensity evaluation device comprising:
a diastolic time measurement section which noninvasively measures cardiac diastolic time of a subject during exercise; and
a diastolic time change detection section which detects a change in the diastolic time which is measured at each measurement time by the diastolic time measurement section and is input to the diastolic time change detection section.

29. The exercise load intensity evaluation device as defined in claim 28, further comprising:
an exercise load intensity measurement section which measures exercise load intensity of the subject,
wherein the diastolic time change detection section detects a change in the diastolic time corresponding to different degrees of exercise load intensity based on output from the exercise load intensity measurement section.

30. The exercise load intensity evaluation device as defined in claim 28,
   wherein the diastolic time measurement section includes an electrocardiogram measurement section which measures an electrocardiogram of the subject during exercise, and measures the diastolic time from a feature of the electrocardiogram which reflects the cardiac diastolic time.

31. The exercise load intensity evaluation device as defined in claim 28,
   wherein the diastolic time measurement section includes a pulse wave detection section which is attached to the subject during exercise and noninvasively detects a peripheral pulse wave, and measures the diastolic time from a feature of the pulse wave which reflects the cardiac diastolic time.

32. The exercise load intensity evaluation device as defined in claim 28,
   wherein the diastolic time measurement section includes:
   a pulse wave detection section which is attached to the subject during exercise and noninvasively detects a peripheral pulse wave; and
   a diastolic time correction section which corrects the cardiac diastolic time based on output from the pulse wave detection section.

33. The exercise load intensity evaluation device as defined in claim 31,
   wherein the diastolic time measurement section further includes:
   a body movement waveform detection section which detects a body movement waveform according to body movement of the subject during exercise; and
   a body movement waveform removal section which removes the body movement waveform detected by the body movement waveform detection section from the pulse wave detected by the pulse wave detection section, and
   wherein the diastolic time measurement section measures the diastolic time based on the pulse wave from which the body movement waveform has been removed.

34. The exercise load intensity evaluation device as defined in claim 31,
   wherein the diastolic time measurement section measures the diastolic time by subtracting ejection duration from rise of the pulse wave to a dicrotic notch from one cycle of the pulse wave.

35. The exercise load intensity evaluation device as defined in claim 31,
   wherein the diastolic time measurement section includes a first differentiation section which differentiates the pulse wave; and a second differentiation section which differentiates the pulse wave differentiated by the first differentiation section, and measures the diastolic time based on the pulse wave differentiated by the second differentiation section.

36. The exercise load intensity evaluation device as defined in claim 31,
   wherein the diastolic time measurement section includes a comparator which compares a wave height of the pulse wave with a reference value, measures cardiac ejection duration based on a pulse width of a rectangular wave output from the comparator, and measures the diastolic time by subtracting the ejection duration from one cycle of the pulse wave.

37. The exercise load intensity evaluation device as defined in claim 36,
   wherein the comparator is a comparator with hysteresis and having a positive input terminal which is connected with a feed back resistor.

38. The exercise load intensity evaluation device as defined in claim 31,
   wherein the diastolic time measurement section further includes a Fourier transformation section which transforms the pulse wave detected by the pulse wave detection section,
   wherein the diastolic time measurement section extracts a frequency spectrum which is obtained based on the feature of the pulse wave which reflects the cardiac diastolic time from Fourier transformed frequency spectra, and
   wherein the diastolic time change detection section detects a change in frequency of the frequency spectrum extracted at each measurement time by the diastolic time measurement section.

39. The exercise load intensity evaluation device as defined in claim 33,
   wherein the diastolic time measurement section further includes:
   a first Fourier transformation section which transforms the pulse wave detected by the pulse wave detection section; and
   a second Fourier transformation section which transforms the body movement waveform detected by the body movement waveform detection section, and
   wherein the body movement waveform removal section subtracts frequency spectra at the same frequency among frequency spectra in each frequency band output from the first and second Fourier transformation sections.

40. The exercise load intensity evaluation device as defined in claim 39,
   wherein the diastolic time measurement section extracts a frequency spectrum which is obtained based on the feature of the pulse wave which reflects the cardiac diastolic time from frequency spectra output from the body movement waveform removal section, and
   wherein the diastolic time change detection section detects a change in frequency of the frequency spectrum extracted at each measurement time by the diastolic time measurement section.

41. The exercise load intensity evaluation device as defined in claim 39,
   wherein the diastolic time measurement section includes an inverse Fourier transformation section which performs inverse Fourier transformation of output from the body movement waveform removal section; a first differentiation section which differentiates the pulse wave which has been inverse-Fourier-transformed; and a second differentiation section which differentiates the pulse wave differentiated by the first differentiation section, and measures the diastolic time based on the pulse wave differentiated by the second differentiation section.

42. The exercise load intensity evaluation device as defined in claim 28, further comprising:
   a notification section which notifies the subject when the exercise load intensity exceeds a lactate threshold based on output from the diastolic time change detection section.

43. The exercise load intensity evaluation device as defined in claim 28, further comprising:

a notification section which notifies the subject when the exercise enters anaerobic exercise based on output from the diastolic time change detection section.

44. An exercise load intensity evaluation device comprising:
- a diastolic time measurement section which noninvasively measures cardiac diastolic time of a subject during exercise;
- a storage section which stores correlation data between the diastolic time and exercise load intensity; and
- an exercise load intensity detection section which detects the exercise load intensity from the storage section based on the diastolic time measured by the diastolic time measurement section.

45. The exercise load intensity evaluation device as defined in claim 44, further comprising:
- a diastolic time change detection section which detects a change in the diastolic time which is measured at each measurement time by the diastolic time measurement section and is input to the diastolic time change detection section,
- wherein the exercise load intensity detection section detects the exercise load intensity when the diastolic time change detection section detects that the diastolic time is changed.

46. The exercise load intensity evaluation device as defined in claim 28,
- wherein a ratio of the diastolic time to one cycle of a heartbeat is used as an index instead of the diastolic time.

47. The exercise load intensity evaluation device as defined in claim 28,
- wherein the diastolic time change detection section outputs one cycle of a heartbeat when the diastolic time changes.

48. The exercise load intensity evaluation device as defined in claim 42,
- wherein the notification section includes a storage section which stores the diastolic time exceeding a safe exercise range, and notifies the subject that the exercise load intensity is out of the safe exercise range when the measured diastolic time is smaller than the diastolic time stored in the storage section.

49. Exercise equipment comprising the exercise load intensity evaluation device as defined in claim 28.

50. The exercise equipment as defined in claim 49,
- wherein a range of the exercise load intensity is set as a range of a heart rate based on one cycle of a heartbeat output from the diastolic time change detection section.

51. The exercise equipment as defined in claim 49, further comprising:
- an output section which outputs exercise menus of different degrees of exercise load intensity.

52. The exercise equipment as defined in claim 49, further comprising:
- a load output section which outputs exercise load which is applied to the subject according to an exercise menu at different degrees of exercise load intensity.

53. The exercise equipment as defined in claim 51,
- wherein each of the exercise menus is set in a predetermined exercise load intensity range based on a lactate threshold calculated for the subject from a correlation between the exercise load intensity and the diastolic time.

54. The exercise equipment as defined in claim 53,
- wherein a storage medium which stores the exercise menus is removable from the exercise equipment.

* * * * *